US012638451B2

(12) United States Patent
Han

(10) Patent No.: US 12,638,451 B2
(45) Date of Patent: May 26, 2026

(54) GENETIC AMPLIFIED TUMOR HOMING NANOPARTICLES AND COMPOSITIONS AND METHODS THEREOF

(71) Applicant: University of Massachusetts, Boston, MA (US)

(72) Inventor: Gang Han, Shrewsbury, MA (US)

(73) Assignee: University of Massachusetts, Westborough, MA (US)

( * ) Notice: Subject to any disclaimer, the term of this patent is extended or adjusted under 35 U.S.C. 154(b) by 1169 days.

(21) Appl. No.: 17/602,765

(22) PCT Filed: May 21, 2020

(86) PCT No.: PCT/US2020/033909
§ 371 (c)(1),
(2) Date: Oct. 10, 2021

(87) PCT Pub. No.: WO2020/236998
PCT Pub. Date: Nov. 26, 2020

(65) Prior Publication Data
US 2022/0178928 A1 Jun. 9, 2022

Related U.S. Application Data

(60) Provisional application No. 62/850,886, filed on May 21, 2019.

(51) Int. Cl.
*G01N 33/574* (2006.01)
*C12N 15/86* (2006.01)
*G01N 33/57555* (2026.01)

(52) U.S. Cl.
CPC ....... *G01N 33/57555* (2026.01); *C12N 15/86* (2013.01); *C12N 2710/10343* (2013.01); *C12N 2830/002* (2013.01); *G01N 2333/705* (2013.01)

(58) Field of Classification Search
CPC .............. G01N 33/57434; C12N 15/86; C12N 15/861; C12N 2710/10343; C12N 2830/002
See application file for complete search history.

(56) References Cited

FOREIGN PATENT DOCUMENTS

WO WO-2009033176 A1 * 3/2009 ....... A61K 39/39558

OTHER PUBLICATIONS

Weissleder R, et al. In vivo magnetic resonance imaging of transgene expression. Nat Med. Mar. 2000;6(3):351-5. doi: 10.1038/73219. PMID: 10700241. (Year: 2000).*
Ding M, et al. Prostate cancer-specific and potent antitumor effect of a DD3-controlled oncolytic virus harboring the PTEN gene. PLoS One. 2012;7(4):e35153. doi: 10.1371/journal.pone.0035153. Epub Apr. 11, 2012. PMID: 22509396; PMCID: PMC3324420. (Year: 2012).*
Vectors 101 | ASGCT—American Society of Gene & Cell Therapy | downloaded on Mar. 5, 2025.*

(Continued)

*Primary Examiner* — Terra C Gibbs
(74) *Attorney, Agent, or Firm* — Milstein Zhang & Wu LLC

(57) ABSTRACT
The invention provides novel genetic probes and bioactive agents and compositions and methods of use thereof in diagnostic and therapeutic applications.

4 Claims, 22 Drawing Sheets

A schematic illustration of the synergistic gene-nano strategy utilized to enhance the Tf-conjugated nanoparticle tumor-homing in prostate cancer (PCa). Due to the unique tissue-specificity of the DD3 promoter for PCa, the constructed gene probe, namely P$_{DD3}$-TfR-WPRE-P$_{CMV}$-Luc, significantly upregulates the expression of TfR and Luc only in the PCa cells (A). As a result, the elevated TfR proteins on the tumor cells mediated by the genetic probes could significantly enhance the tumor-targeting ability and simultaneously minimize the off-targeting of Tf-conjugated nanoprobes (B).

(56)                    References Cited

OTHER PUBLICATIONS

Generative artificial intelligence (AI) from Google AI Overview downloaded from do all vectors behave the same—Google Search on Mar. 5, 2025.*
Generative artificial intelligence (AI) from Google AI Overview downloaded from are retrovirus, adenovirus and lentivirus vectors the same—Google Search on Mar. 5, 2025.*
Ding et al. (PLOS One, vol. 7, No. 4, Apr. 11, 2012 p. e35153, 1-11).*
Zhao et al. (Adv. Mater. 2019, vol. 31, 1900928, pp. 1-8).*

* cited by examiner

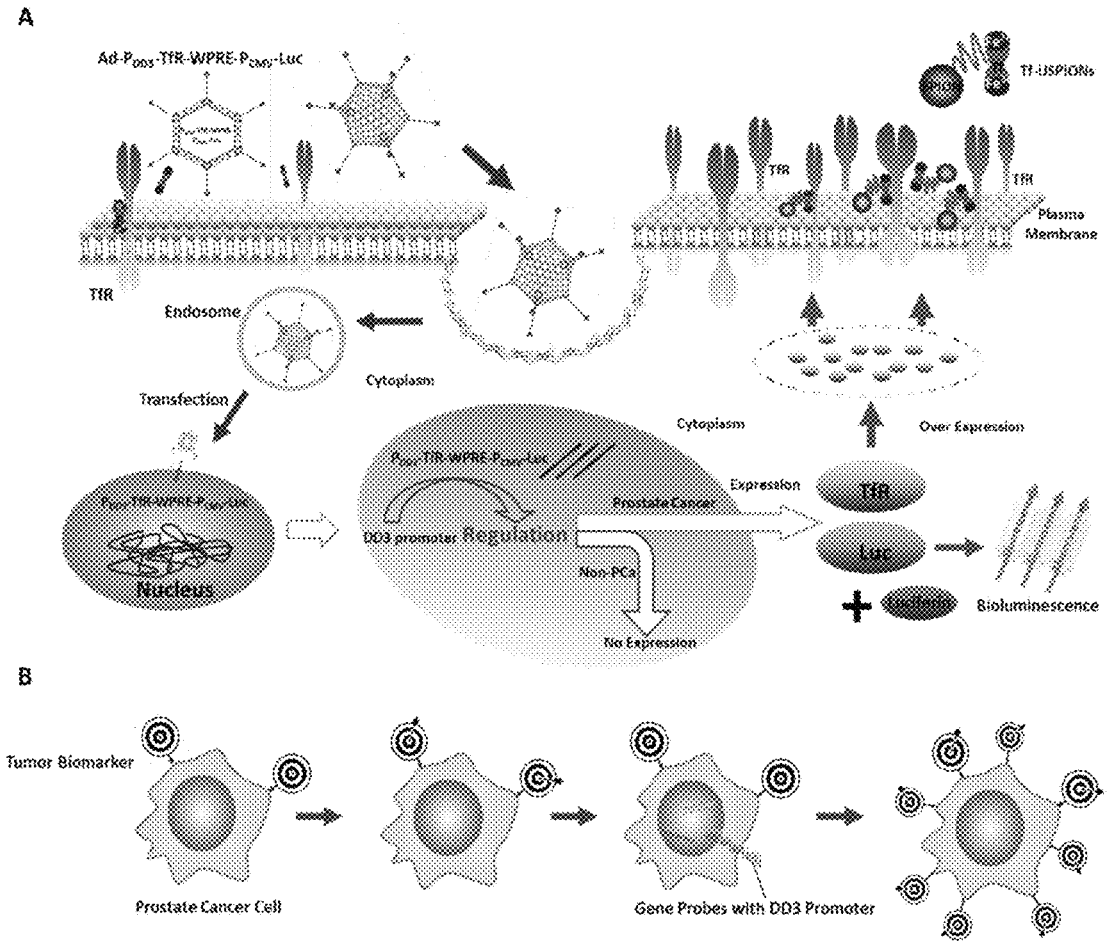

FIG. 1. A schematic illustration of the synergistic gene-nano strategy utilized to enhance the Tf-conjugated nanoparticle tumor-homing in prostate cancer (PCa). Due to the unique tissue-specificity of the DD3 promoter for PCa, the constructed gene probe, namely $P_{DD3}$-TfR-WPRE-$P_{CMV}$-Luc, significantly upregulates the expression of TfR and Luc only in the PCa cells (A). As a result, the elevated TfR proteins on the tumor cells mediated by the genetic probes could significantly enhance the tumor-targeting ability and simultaneously minimize the off-targeting of Tf-conjugated nanoprobes (B).

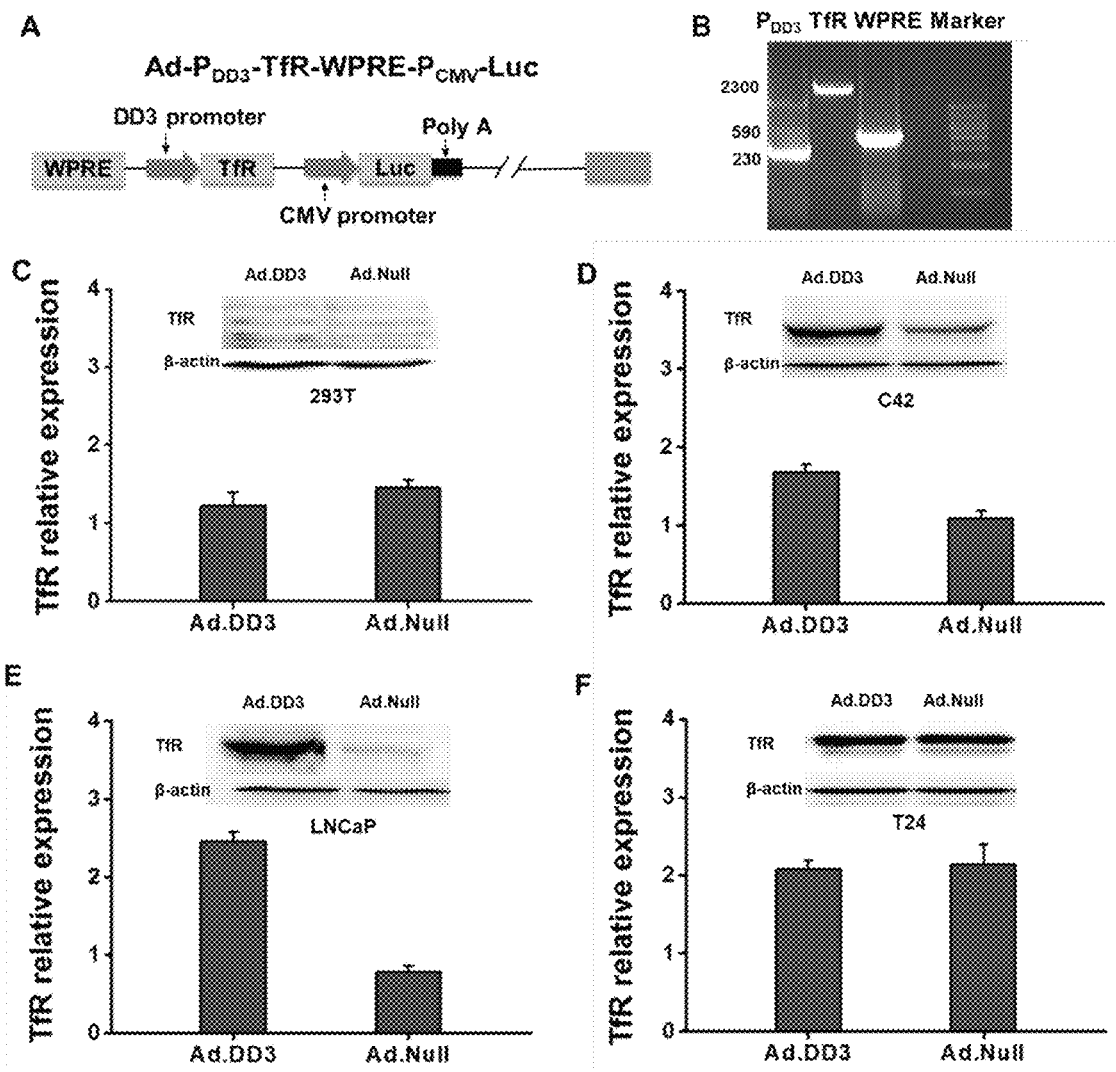

FIG. 2. Characterization of $P_{DD3}$-TfR-WPRE-$P_{CMV}$-Luc. (A) A schematic diagram of the constructed gene probe, in which the expression of the TfR gene was regulated by the PCa-specific DD3 promoter and the WPRE enhancer. The expression cassette of Luc, as driven by the DD3 and CMV promoter together, was inserted downstream of the TfR gene to non-invasively visualize the TfR expression. (B) The structure of the constructed gene probes verified by PCR using sets of primers corresponding to several important regions of the generated virus. The relative expression of the TfR gene measured by Western blot analysis in 293T cells (C), C42 cells (D), LNCaP cells (E), and T24 cells (F) after infection with Ad.$P_{DD3}$-TfR-WPRE-$P_{CMV}$-Luc (Ad.DD3) or Ad.Null (a negative control). β-actin was used as the internal control.

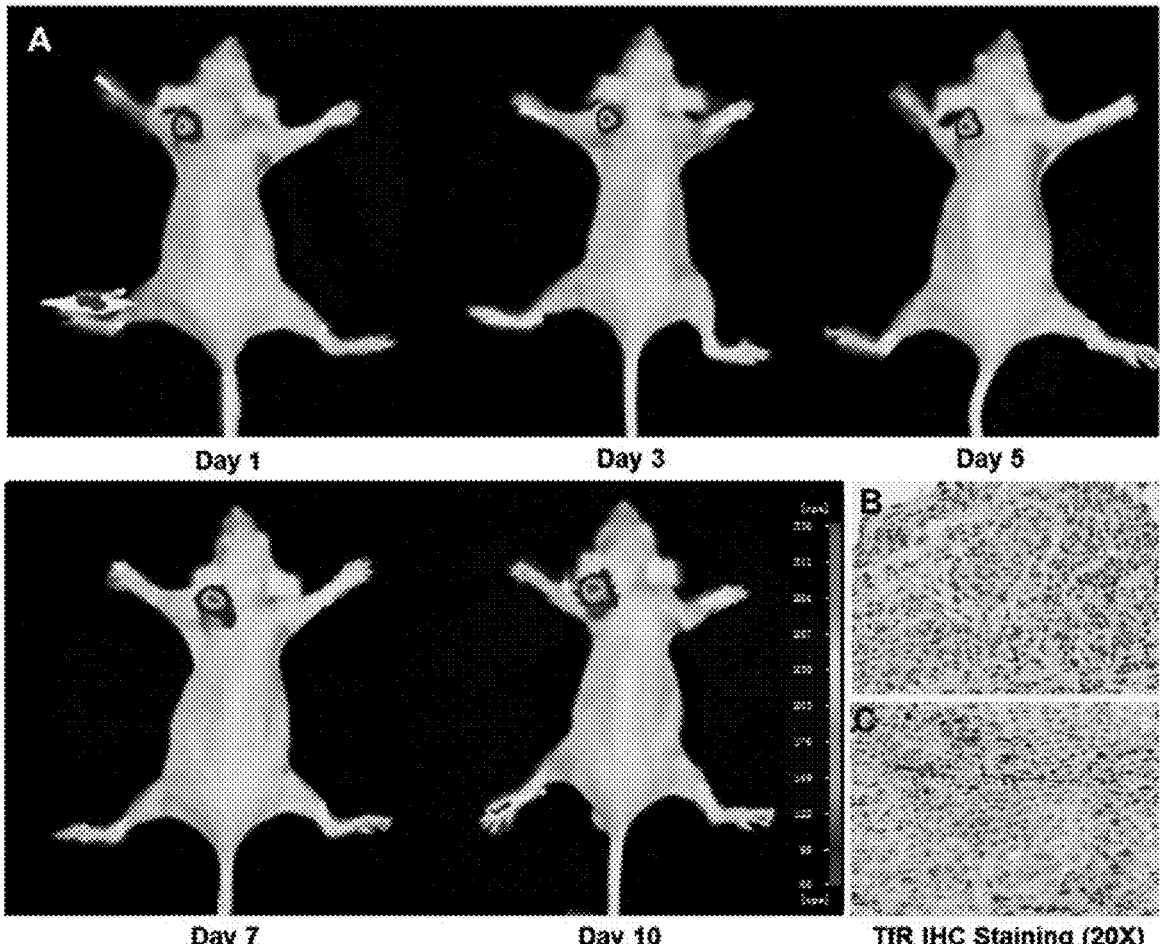

FIG. 3. (A) Tumor-targeted bioluminescence imaging of LNCaP tumor-bearing mice after injection of Ad.DD3 demonstrate the specific expression pattern of the constructed Ad.DD3 in prostate tissue. The IHC staining of TfR expression at 7 days after the mice were treated with Ad.DD3 (B) or PBS (C), shows that Ad.DD3-treated tumors expressed significantly higher TfR than the PBS-treated tumors.

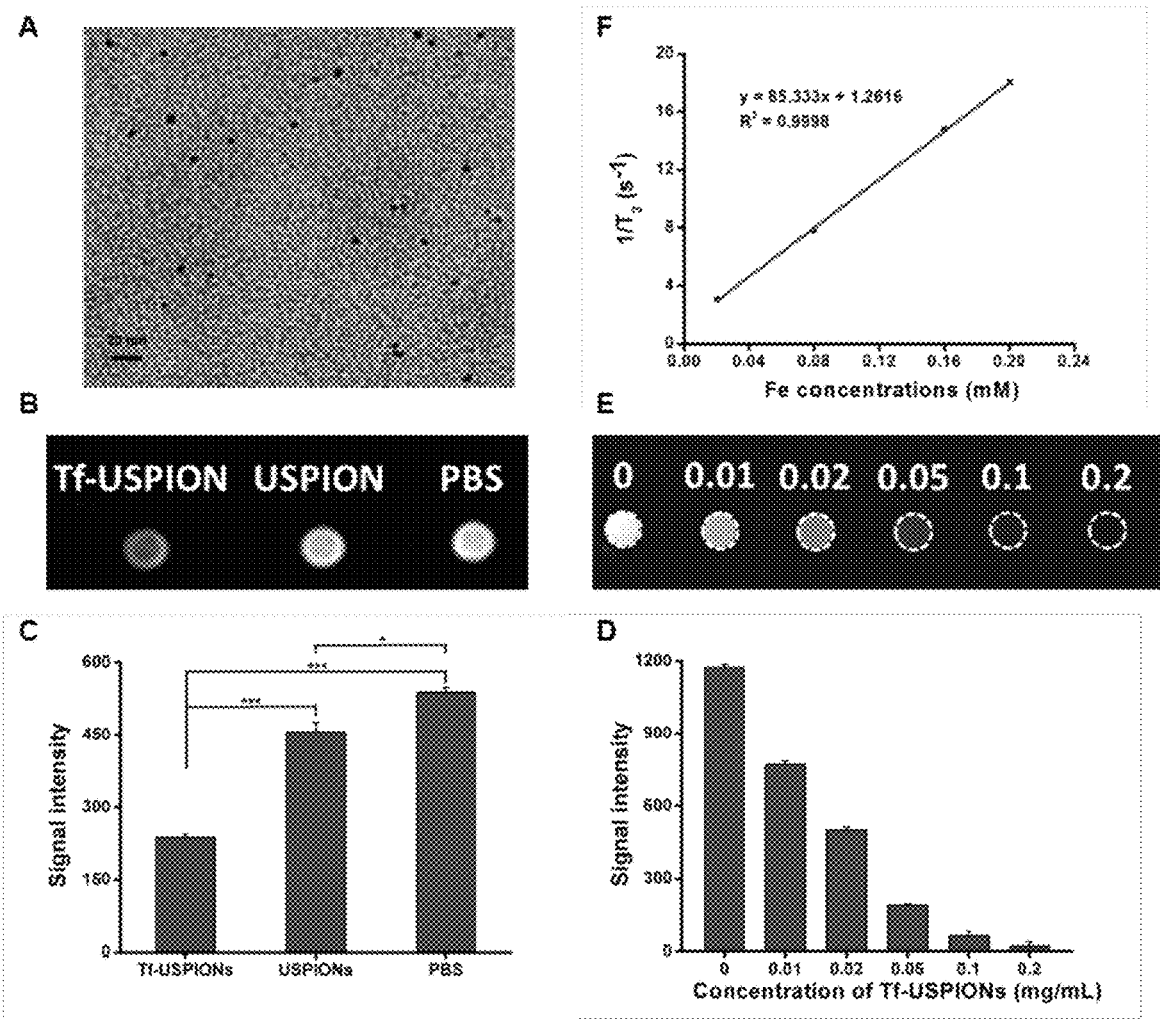

FIG. 4. Characterization of Tf-USPIONs. (A) HRTEM images of Tf-USPIONs. Scale bar: 20 nm. In vitro T2-weighted MR images (B) and their signal intensity (C) of LNCaP cells after incubation with Tf-USPIONs, USPIONs and PBS, respectively. T2-weighted MR images of Tf-USPIONs solution (D) and their signal intensity (E) at the Fe concentrations of 0, 0.01, 0.02, 0.05, 0.1 and 0.2 mM, respectively. (F) A linear fitting of 1/T2 with respect to Fe concentrations, indicating the T2 relaxivity value of the prepared nanoprobes was $85.33 \text{mM}^{-1}\text{S}^{-1}$. $***P < 0.0001$ for Tf-USPIONs versus USPIONs and PBS.

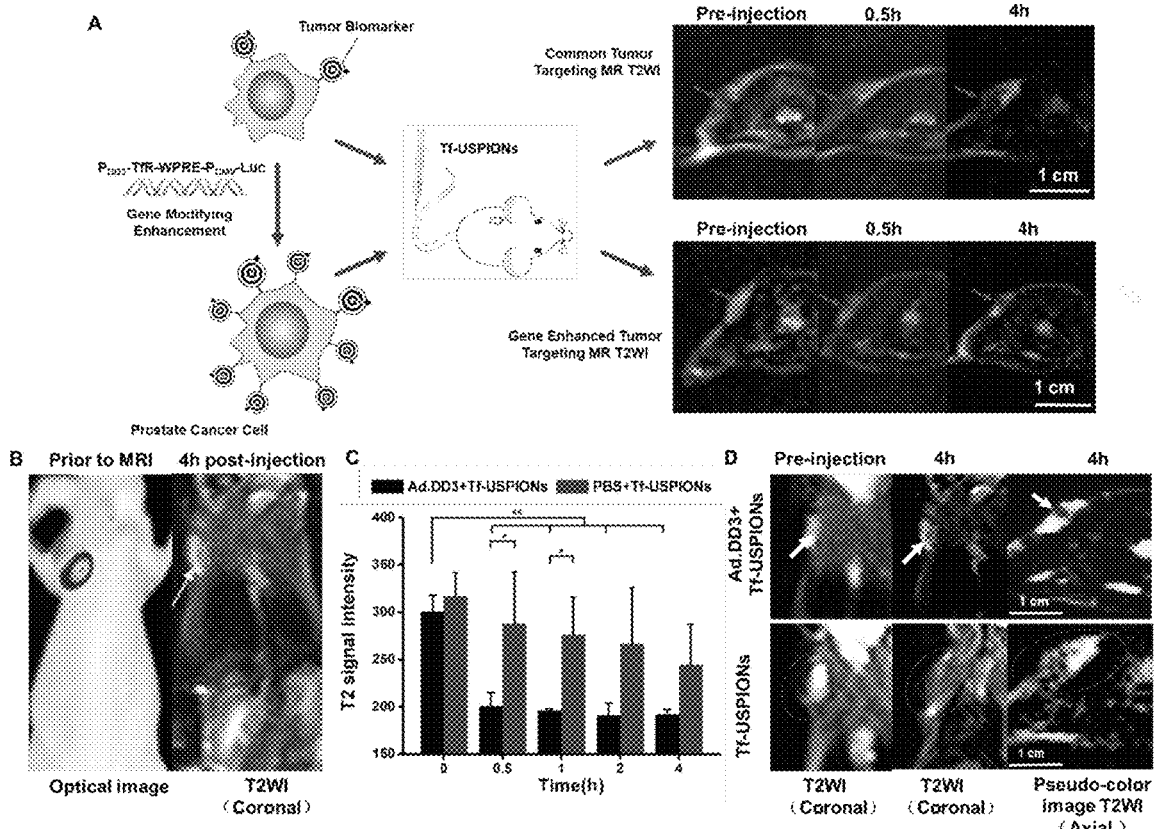

FIG. 5. (A) T2 weighted MR imaging of tumor-bearing mice before and after the treatment of Ad.DD3+Tf-USPIONs or single Tf-USPIONs. (B) The coronal T2 weighted images of Ad.DD3-infected tumors after the injection of Tf-USPIONs and their bioluminescent images prior to MR imaging. (C) The statistical analysis of the T2 signal intensity of tumors before and after being treated with Ad.DD3+Tf-USPIONs or Tf-USPIONs using Student's t test. Note: *p<0.05, and **p<0.005. (D) T2-weighted MR images and their pseudo-color images at 4h post-injection of Tf-USPIONs into the Ad.DD3-infected or un-infected tumors.

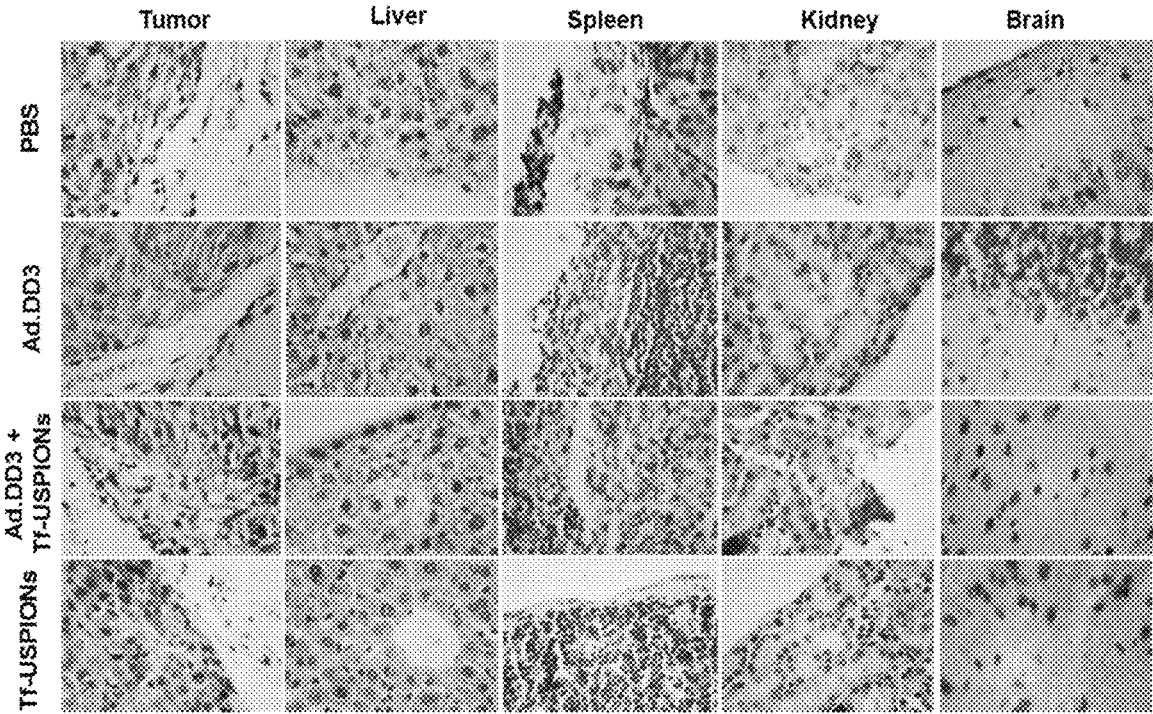

FIG. 6. Images of H&E-stained sections of tumors and normal organs from different treatment groups. No histological changes were visualized in the tumor, liver, spleen, kidney, brain, heart, or lung at 2 weeks after treatment with PBS, Ad.DD3, Ad.DD3+Tf-USPIONs or PBS+Tf-USPIONs stained sections demonstrated the good in vivo biosafety of the combined application of Ad.DD3 with Tf-USPIONs. The magnifications were 40X.

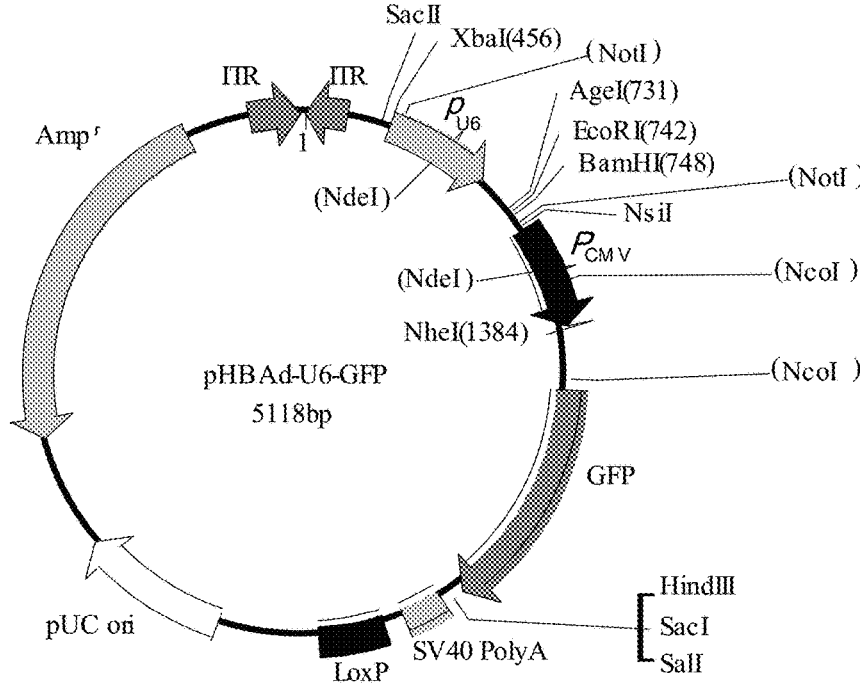
FIG. 7. A schematic diagram of the adenoviral shuttle vector pHBAd-U6-GFP that was used for the construction of Ad.DD3.

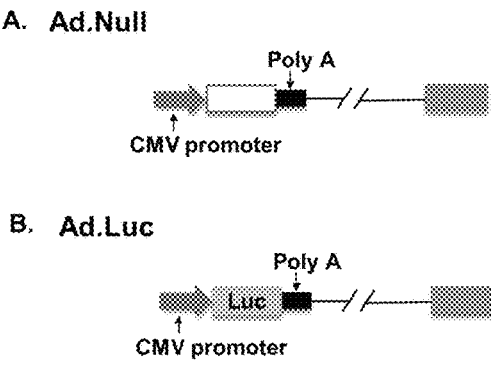

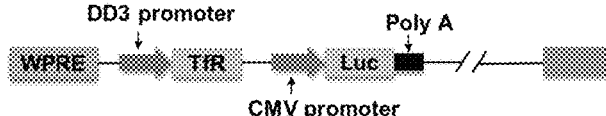

FIG. 8. Schematic diagrams of Ad.Null (A), Ad.Luc (B) and Ad.DD3 (C). Ad.Null and Ad.Luc were a kind gift from Hanbio (Shanghai) Biotechnology Co., Ltd and used as control. Ad.Null is an empty adenovirus under the constitute CMV promoter. That's to say, no expression cassettes like Luc and TfR gene were inserted into the downstream of the CMV promoter in Ad.Null. Ad.Luc can express the Luc gene under the constitute CMV promoter in both PCa tumors and non-Pca tissues.

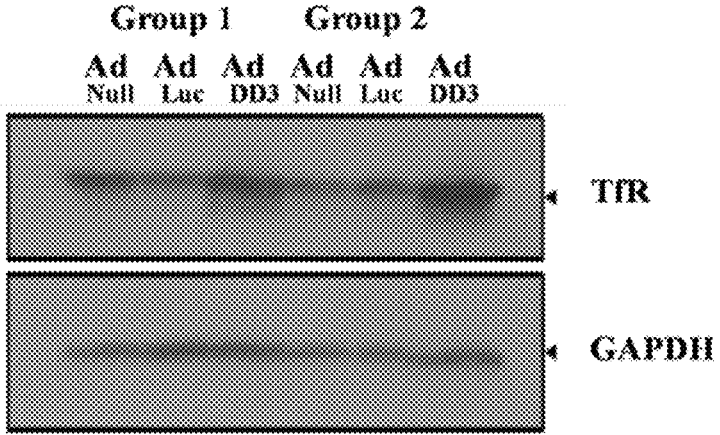

FIG. 9. A western blot analysis of TfR expression in LNCaP cells 24 hours after being infected with Ad.Null, Ad. Luc, and Ad.DD3. GAPDH was set as the internal reference.

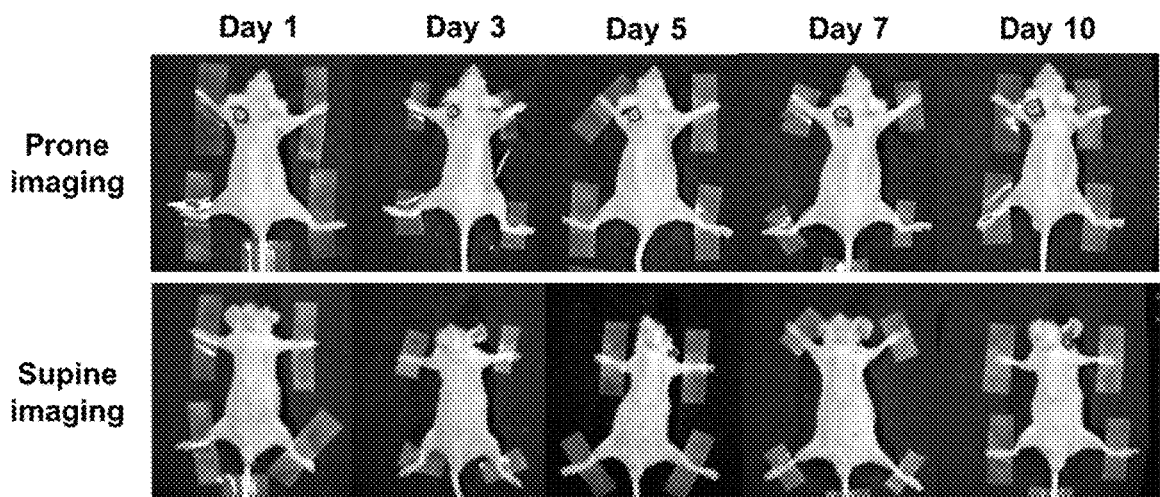

FIG. 10. The prone and supine bioluminescence imaging of the LNCaP xenograft tumor-bearing nude mice after being infected with Ad.DD3. The bioluminescence signal derived from the Luc reporter of Ad.DD3 was only visualized in tumor regions, which non-invasively demonstrates the specific-targeted expression pattern of Ad.DD3 *in vivo*.

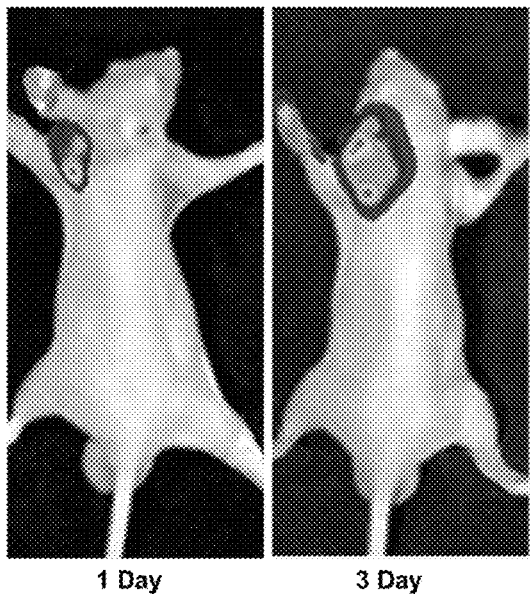

FIG. 11. The bioluminescence imaging of LNCaP xenograft tumor-bearing nude mice after the treatment of Ad.Luc. The bioluminescent signal was observed in the tumors and their surrounding tissues. Meanwhile, the bioluminescent range enlarged over time, with no correlation to tumor sizes.

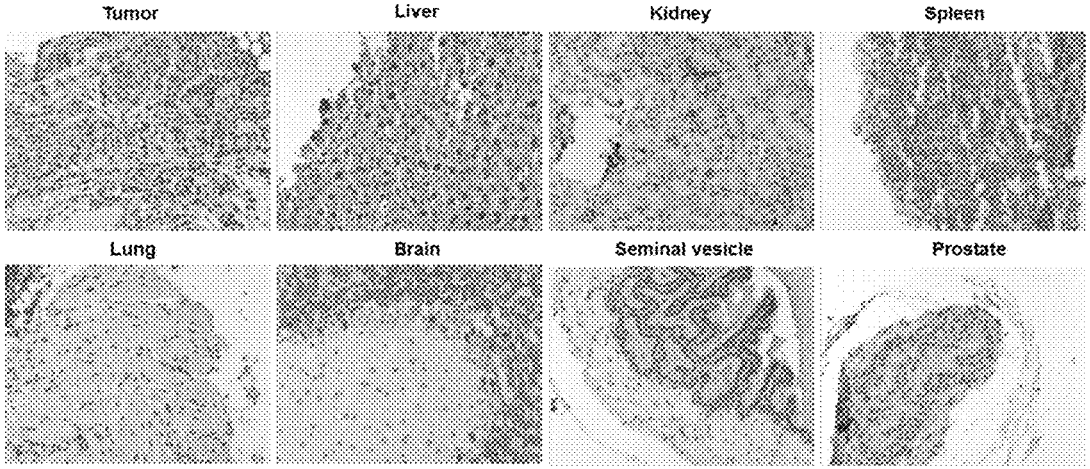

FIG. 12. The immunostaining analysis of TfR expression in different normal organs after the LNCaP xenograft tumor-bearing nude mice were treated with Ad.DD3. No obvious Tf expression was observed in the normal tissues, including the liver, kidney, spleen, lung, brain and prostate. Compared with the remarkably elevated expression of TfR that was detected in the Ad.DD3-infected tumor tissues, this immunostaining analysis confirmed the tumor-specific function of Ad.DD3 to up-regulate TfR expression in prostate cancer. Magnifications, 20X.

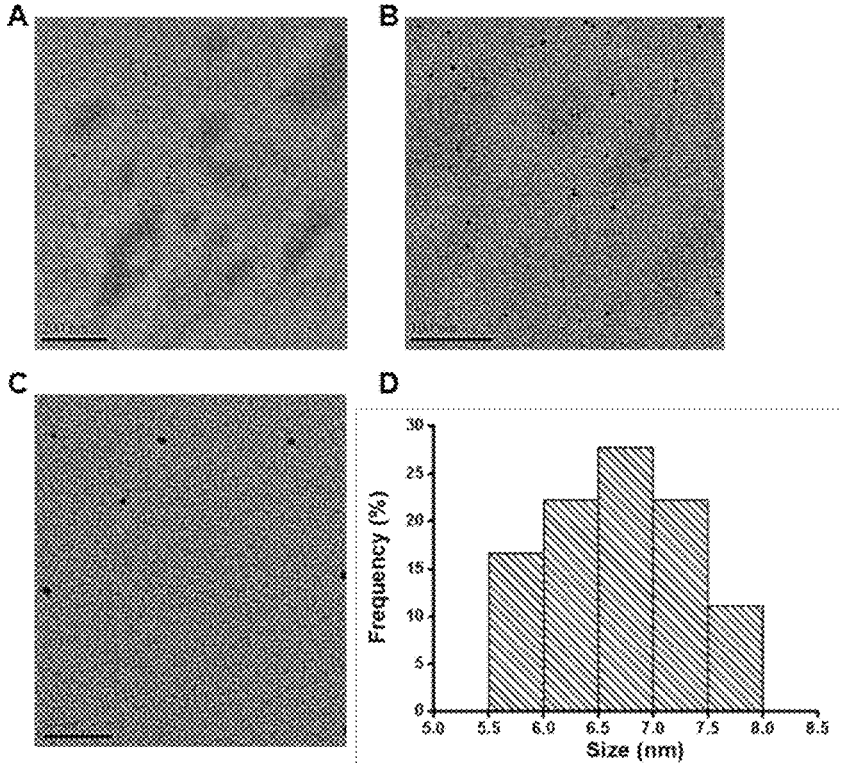
FIG. 13. TEM image of the USPIONs at different scale bars [(A) 200 nm, (B)100 nm, and (C)50 nm], and their size distribution (D). The as-prepared USPIONs were spherical, monodisperse and uniform, with an average size of approximately 6 nm.

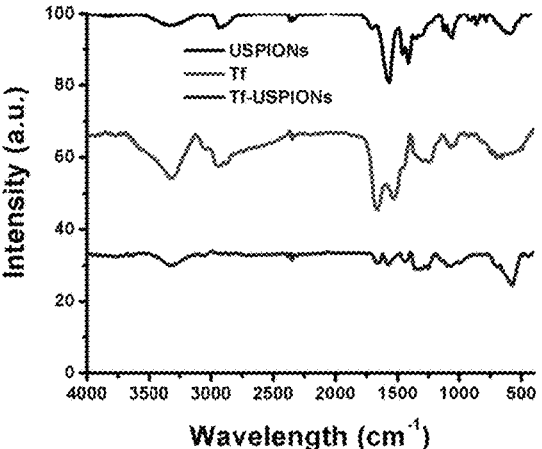

FIG. 14. FTIR spectra of Tf-USPIONs, demonstrating the successful conjugation of Tf and USPIONs.The spectrum for carboxylated USPIONs showed two peaks at 1550 and 1405 cm$^{-1}$, which were attributed to the antisymmetrical vibration and symmetric vibration of the COO-groups respectively. However, these peaks redshifted and weakened, while two new peaks at 1630 and 1565 cm$^{-1}$ representing characteristically stretching of vibrations of amide bonds. This result indicated successfully construction of the coupling between the Tf and the carboxylated USPIONs.

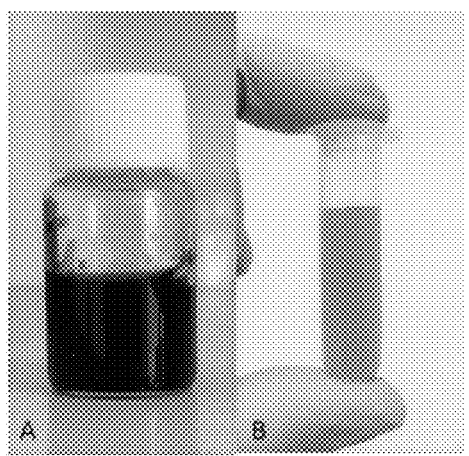

FIG. 15. A photograph of the stock solution (A) and its diluted sample during a 2 week storage period. After freeze-drying, the lyophilized Tf-USPIONs could be easily redissolved in PBS in order to obtain different concentrations of Tf-USPIONs solutions. After being stored at room temperature for 2 months, no precipitation was found in these uniformly dark solutions, demonstrating the good colloidal stability and dispersity of the Tf-USPIONs nanoprobes.

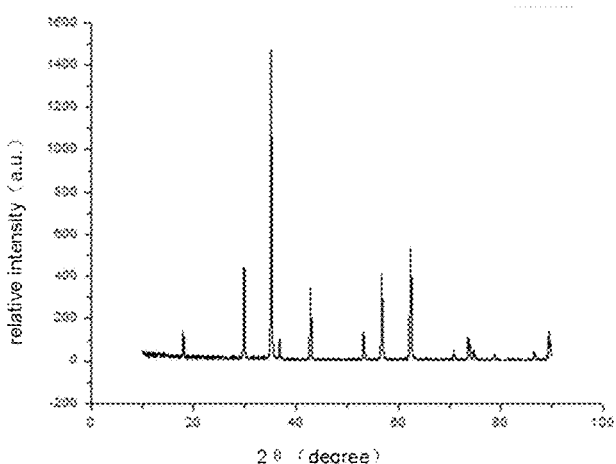

$2\theta$ (degree)

FIG. 16. X-ray powder diffraction (XRD) pattern of the prepared Tf-USPIONs. The diffraction peaks appeared at the Bragg angles $2\theta$ ~30.38°, 35.48°, 43.09°, 53.52°, 57.14°, and 62.68°. According to JCPDS card no. 19–0629, all the diffraction peaks could be indexed to face-centered cubic phase of $Fe_3O_4$.

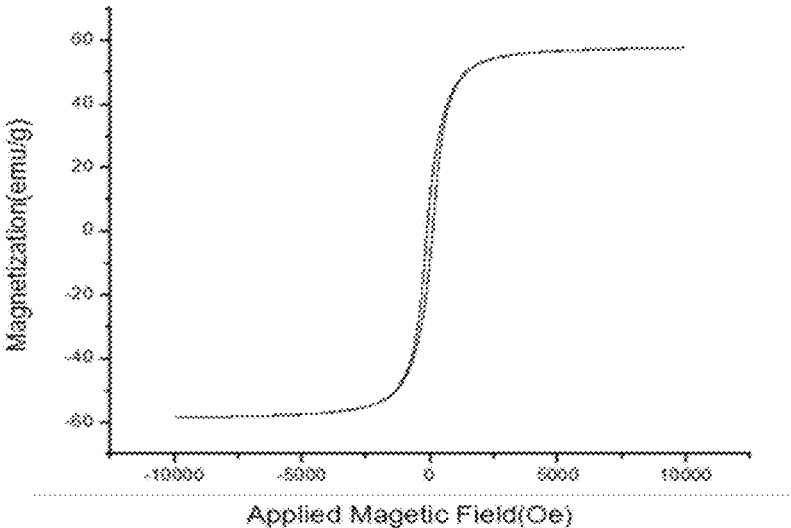

FIG. 17. The magnetic hysteresis loop curves of the prepared Tf-USPIONs nanoprobes, demonstrating the superparamagnetic property of Tf-USPIONs nanoprobes at room temperature.

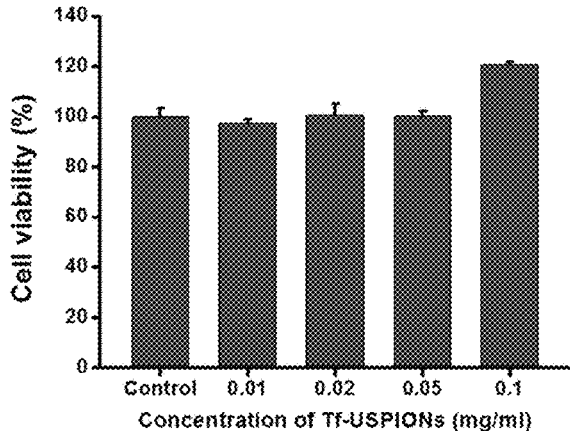

FIG. 18. The MTT cell viability assay under different concentrations of Tf-USPIONs. The results revealed that cell growth was not inhibited by the treatment with Tf-USPIONs, demonstrating the negligible cytotoxicity of the prepared nanoparticles.

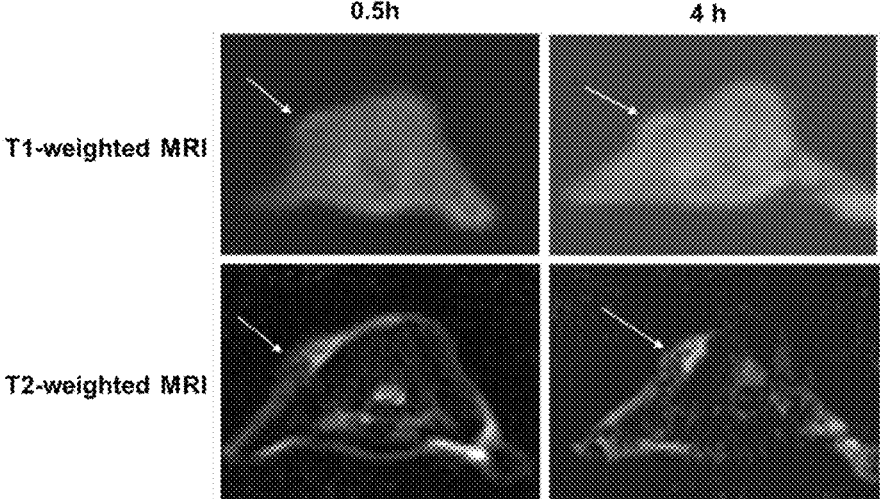
FIG. 19. In vivo MR images of the un-infected LNCaP tumor-bearing mice after intravenous injection of 200 μL Tf-USPIONs (0.5 mg/mL). The arrows indicates he tumor regions.

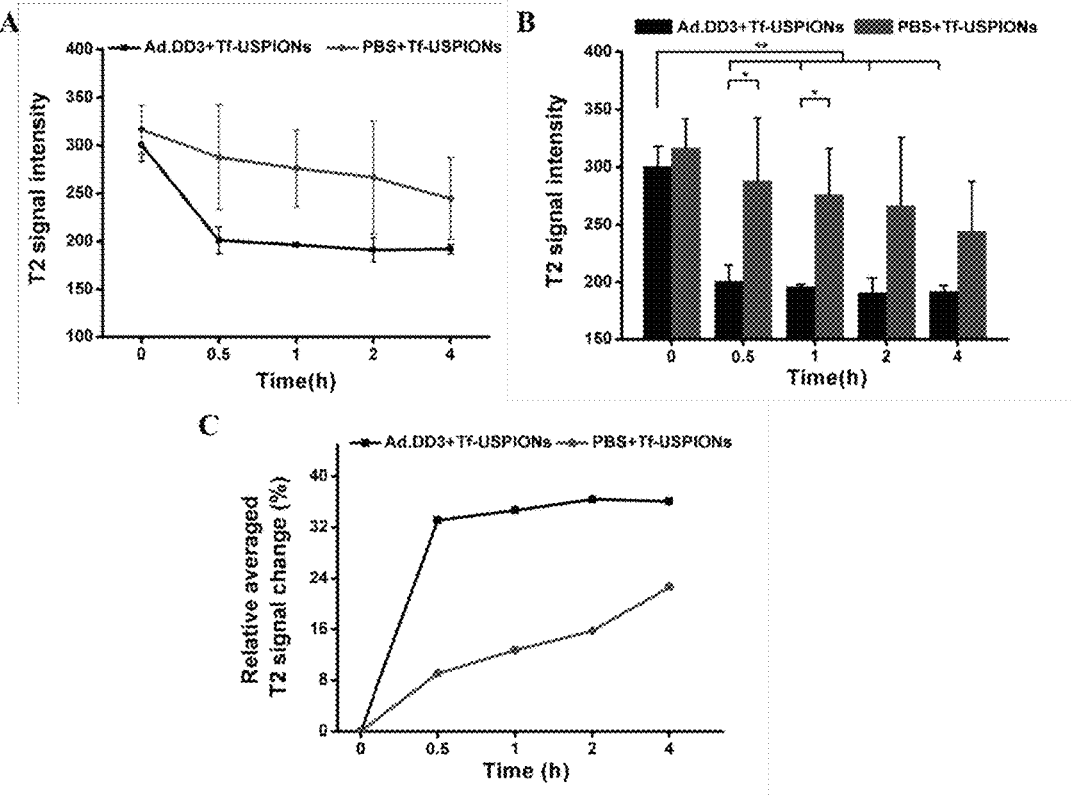

FIG. 20. (A) The T2 signal intensity of tumors before and at 0.5h, 2h, 4h after the treatment of Ad.DD3+Tf-USPIONs. The mice treated with PBS+Tf-USPION were used as control. (B) The statistical analysis of the T2 signal intensity of tumors before and after being treated with Ad.DD3+Tf-USPIONs or PBS+Tf-USPIONs using Student's t test. Note: *p<0.05, and **p<0.005. (C) The average change in the T2 signal intensity of tumors normalized by its baseline level. After treatment with Tf-USPIONs, the Ad.DD3-infected tumors showed more rapid and dramatic T2 signal change than the PBS-treated group.

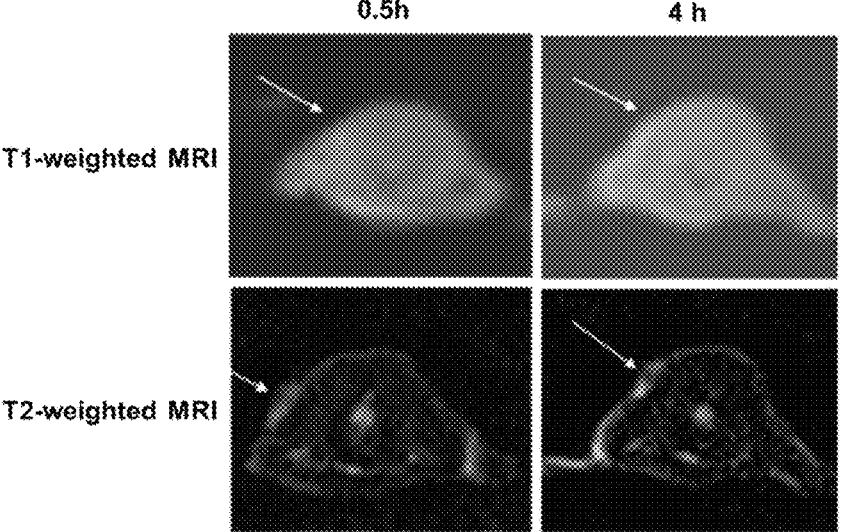
FIG. 21. In vivo MR images of the Ad.DD3-infected LNCaP xenograft tumor-bearing mice after intravenous injection of 200 μL Tf-USPIONs (0.5 mg/mL). The arrows indicate the tumor regions. Transverse T2-weighted MR image at 4 h post-injection of Tf-USPIONs showed a definite boundary between the hypo-intensive tumor mass and its surrounding tissues.

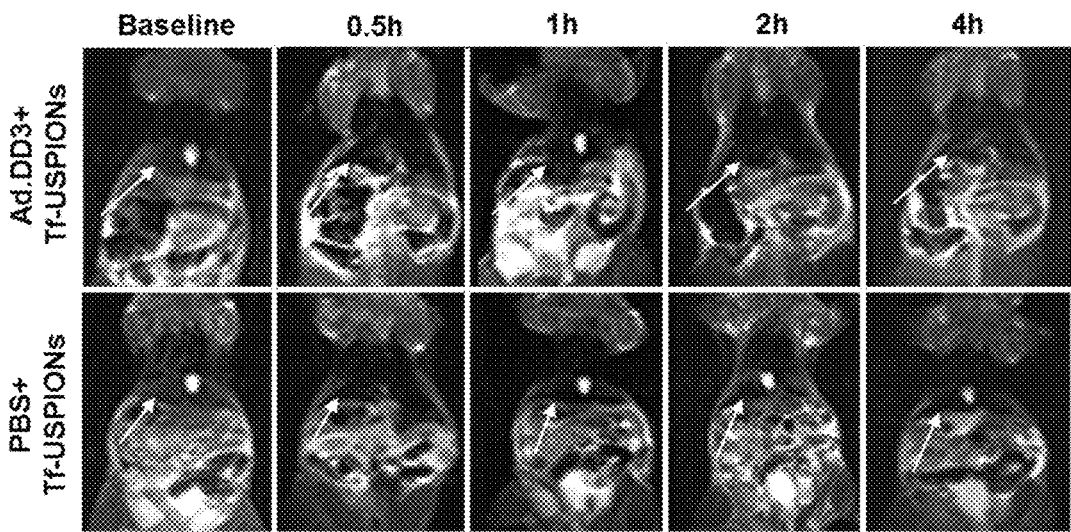

FIG. 22. In vivo T2 weighted MR images of the liver of the Ad.DD3-infected LNCaP xenograft tumor-bearing mice before and after injection of 200 μL Tf-USPIONs (0.5 mg/mL). The mice treated with pure Tf-USPIONs were used as control.

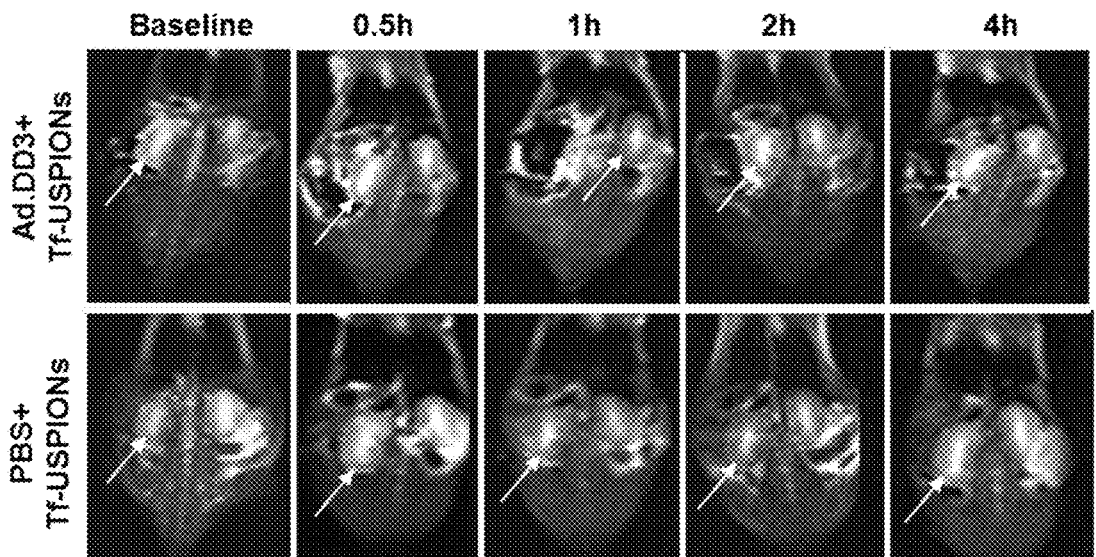

FIG. 23. In vivo T2 weighted MR images of the kidney of the Ad.DD3-infected LNCaP xenograft tumor-bearing mice before and after injection of 200 μL Tf-USPIONs (0.5 mg/mL). The mice treated with pure Tf-USPIONs were used as control.

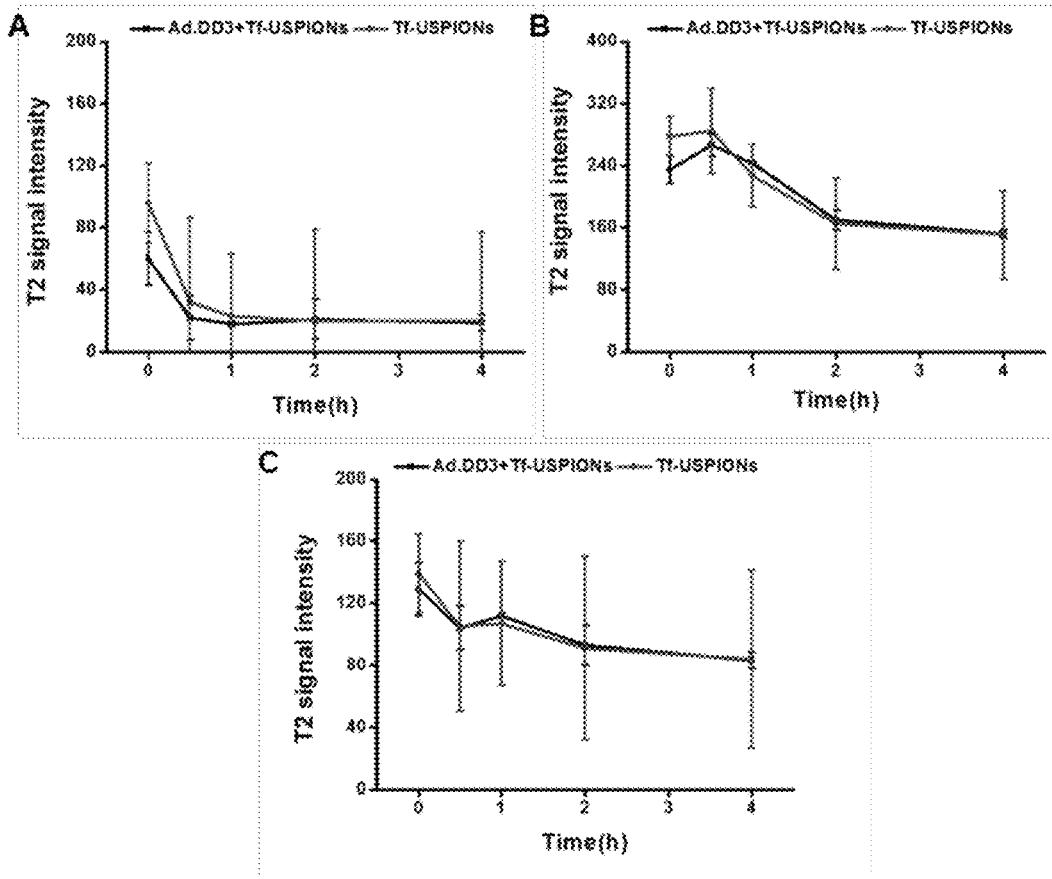
FIG. 24. The T2 signal intensity of livers (A), kidneys (B), and muscles (C) after the injection of Ad.DD3+Tf-USPIONs or pure Tf-USPIONs, respectively.

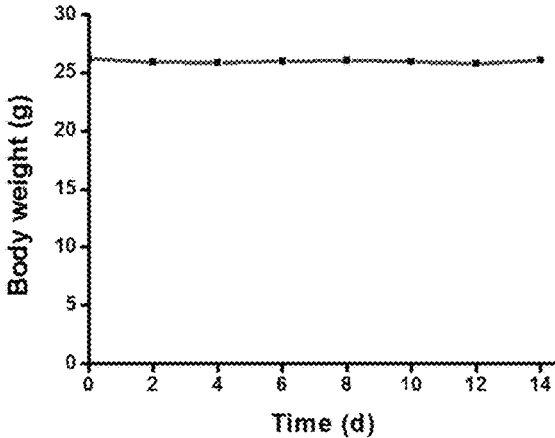

FIG. 25. Body weight changes of the LNCaP xenograft tumor-bearing mice before and after treatment of Ad.DD3 and Tf-USPIONs. The mice were pre-treated with Ad.DD3 on the first day. Subsequently, Tf-USPIONs were injected into the Ad.DD3-infected mice on the eighth day. No significant body weight changes were observed during an observation period of 15 days.

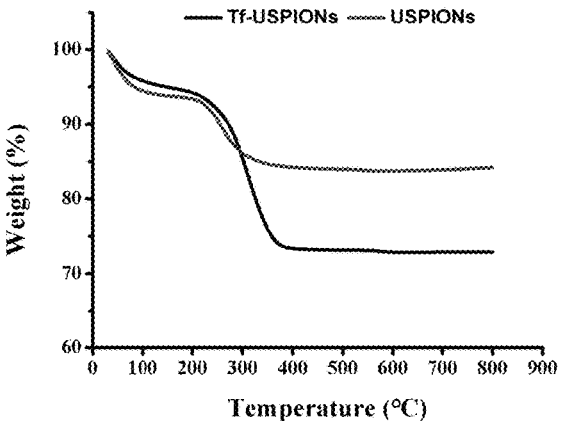

FIG. 26. The TGA curves of USPIONs and Tf-USPIONs.

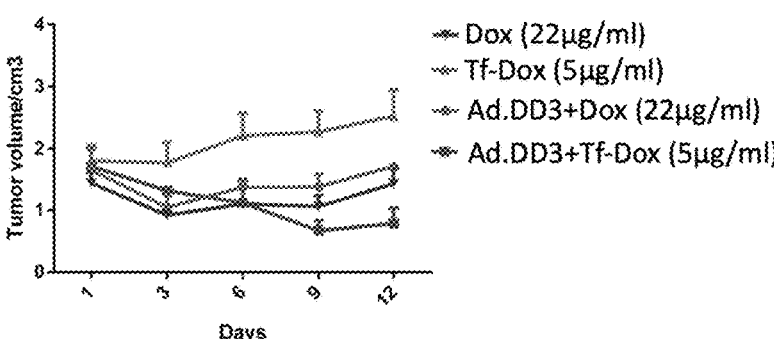
FIG. 27. Changes of tumor volume after different treatment indicated Ad.DD3 enhanced the therapeutic efficacy of Dox in tumor bearing mice.
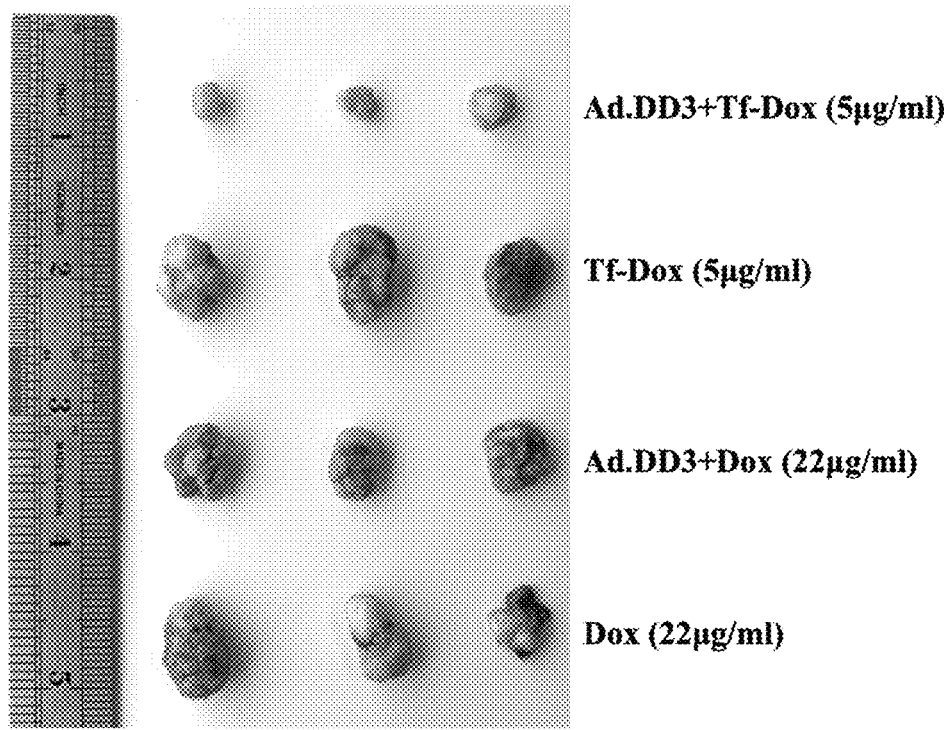
FIG. 28. the tumor masses excised from the mice at 12 days after treatment with Dox, Ad.DD3+Dox, Tf-Dox, and Ad.DD3+Tf-Dox.

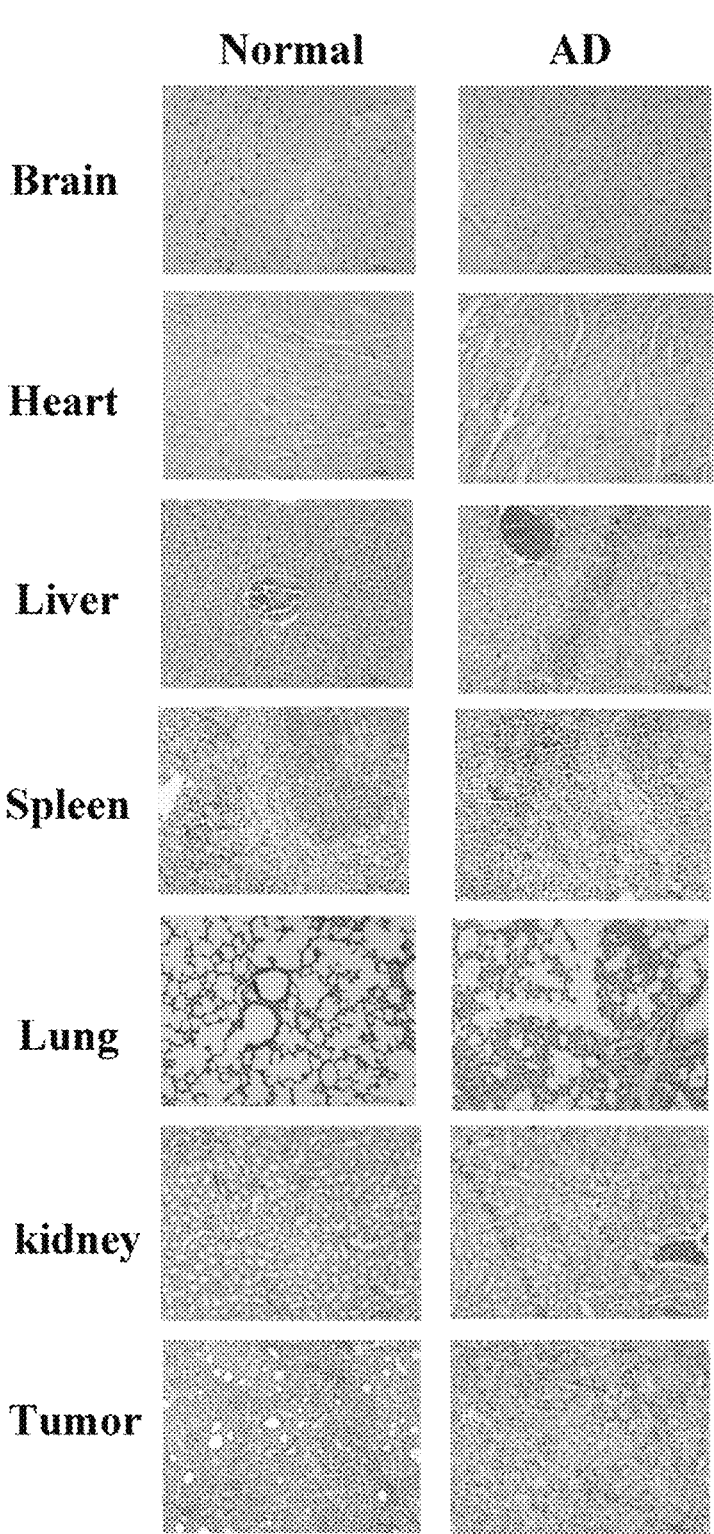
FIG. 29. HE-staining results of tumor-bearing mice after treatment with PBS or Ad.DD3 indicated negligible effect of Ad.DD3 on the histological structure of major organs.

GENETIC AMPLIFIED TUMOR HOMING NANOPARTICLES AND COMPOSITIONS AND METHODS THEREOF

PRIORITY CLAIMS AND RELATED APPLICATIONS

This application is the U.S. national phase of and claims priority to PCT/US20/33909, filed May 21, 2020, which claims the benefit of priority from U.S. Provisional Application Ser. No. 62/850,886, filed on May 21, 2019, the entire content of each of which is incorporated herein by reference.

TECHNICAL FIELDS OF THE INVENTION

The invention generally relates to bioactive agents and compositions thereof. More particularly, the invention provides novel genetic probes and bioactive agents and compositions and methods of use thereof in diagnostic and therapeutic applications.

BACKGROUND OF THE INVENTION

Prostate cancers (PCa) have become the second most commonly diagnosed cancer in the male population worldwide. In the U.S. alone, about 1 of every 6 men will be diagnosed with PCa in his lifetime. Traditional treatment approaches for PCa involve radical whole-gland procedures, such as radical prostatectomy or radiation therapy. However, radical therapy can frequently be associated with considerable morbidity and off-tumor undesired side effects in surrounding healthy tissues, for example, urinary incontinence and erectile dysfunction. (Torre, et al. 2015 *CA Cancer. J Clin.* 65, 87; ACS. Cancer Facts and Figures. Atlanta: ACS; 2010; Resnick, et al. 2013 *N. Engl. J. Med.* 368, 436.)

Such side effects often in turn lead to severe physical and mental health problems beside tumor treatment itself, and thus cause not only secondary suffering in post-operation patients but also surgery fear in many pre-operation patients. Less invasive treatment strategies, such as focal therapy, have therefore received tremendous attention due to the promise of fewer complications for the patient. (Perera, et al. 2016 *Nat. Rev. Urol.* 13, 641.)

In focal therapy, the tumorous prostate regions are ablated and/or excised, while the surrounding normal tissues and their functions can be maximally preserved. The success of focal ablation is greatly dependent on precise visualization of PCa lesions and confidence in the absence of tumor elsewhere, which are the key issues that remain to be addressed for PCa pre-operative diagnosis and subsequent treatment.

To this end, magnetic resonance imaging (MRI) is the most important clinical imaging tool to identify and characterize PCa and respective treatment options. Unfortunately, because more than 60% of PCa are considered multifocal and 30% of lesions occur outside the peripheral zone, existing MRI tools have limitations with regards to their sensitivity and signal contrast between PCa malignancy and the adjacent normal tissues, especially when imaging small and early-stage tumors. (Villers, et al. 1992 *Cancer* 70, 2313; Le, et al. 2015 *EUR UROL* 67, 569; Vargas, et al. 2012 *Radiology* 262, 894; Noguchi, et al. 2000 *J. Urol.* 163, 1751.) Therefore, a lack of imaging tools to accurately estimate the location of a tumor, its volume, and the aggressiveness of individual cancer foci, has greatly restricted the further development of PCa focal therapy.

Scientists have developed various nanoprobes to improve the capacity of MRI to detect PCa. Various ligands specific to PCa are used to conjugate nanoparticles to further amplify the nanoparticle tumor site accumulation since tumor-specific surface antigens or biomarkers and their respective ligands have unique "target-arrow" relationships. (Gallo, et al. 2013 *Chem. Soc. Rev.* 42, 7816; Ceci, et al. 2017 *Methods* 130, 36; Lima-Tenorio, et al. 2015 *Int J Pharm* 493, 313; d) Winter, et al. 2018 *Eur. Urol.* 73, 813; Ghosh, et al. 2012 *Nat Nanotechnol.* 7, 677; Zhao, et al. 2017 *Nano Lett.* 17, 4096; Mangadlao, et al. 2018 *ACS NANO* 12, 3714; Cui, et al. 2017 *Int. J. Nanomedicine* 12, 6787; Souchek, et al. 2018 *Acta Biomaterialia*. doi: 10.1016/j.actbio.2018.06.016.)

For example, transferrin receptor (TfR) is upregulated on the surface of PCa cells. Transferrin (Tf) has become an attractive ligand to target PCa and such Tf-modified nanoprobes are promising in improving MRI detection of PCa. Nevertheless, the expression of TfR is often suboptimal and heterogeneous in certain PCa subtypes. (Zhao, et a. 2017 *Nano Lett.* 17, 4096; Holland, et al. 2012 *Nat. Med.* 18, 1586; Nakase, et al. 2009 *Cancer Lett.* 274, 290; Aggarwal, et al. 2017 *Mol. Cancer Res.* 15, 1221; Kang, et al. 2015 *Mol. Pharm.* 12, 2947; Salvati, et al. 2013 *Nat. Nanotechnol.* 8, 137; Daniels, et al. 2012 *Biochimica et Biophysica Acta (BBA)—General Subjects* 1820, 291; Clark, et al. 2015 *Proc. Nat.l Acad. Sci.* U S. A. 112, 12486; Han, et al. 2010 *Mol. Pharm.* 7, 2156; Panaccio, et al. 1987 *Immunol. Cell Biol.* 65 (Pt 6), 461; Keer, et al. 1990 *J Urol.* 143, 381.)

Moreover, the sensitivity of the existing MR contrast agents is often inadequate. A large number of nanoparticle MRI probes have to be administered and the MR imaging enhancement outcome of these existing nanoprobes themselves remain unsatisfactory to precisely distinguish a small PCa tumor lesion region from the surrounding healthy tissues.

Thus, significant unmet medical needs and technical challenges remain for detection probes and methods that significantly improve PCa diagnosis accuracy and treatment outcome.

SUMMARY OF THE INVENTION

The invention provides novel genetic probes and bioactive agents, and compositions and methods of use thereof, useful in cancer diagnostic and therapeutic applications.

A synergetic genetic-nanoparticle tumor homing approach is disclosed herein that significantly amplifies Tf-conjugated ultrasmall superparamagnetic nanoparticle PCa tumor homing and its concomitant MR imaging identification. Ultrasmall PCa lesion (e.g., less than 5 mm) can be rapidly and accurately detected using the disclosed method. The invention thus provides a new foundation that enables a major boosting of the MRI effects for a wide variety of commonly used nanoparticle probes that have been otherwise limited. Additionally, significant increase of TfR on PCa cell surfaces offer improved access to diseased cells with improved therapeutic outcome.

In one aspect, the invention generally relates to a genetic probe for specific upregulation of TfR expression level in an infected PCa cell without upregulating TfR expression level in a nonmalignant prostate cell, wherein the genetic probe comprises a promoter of differential display code 3 (DD3) gene and TfR gene and upregulation of TfR expression level results in an increase of TfR level on the PCa cell's surface.

In another aspect, the invention generally relates to a PCa cell infected with a genetic probe disclosed herein.

In yet another aspect, the invention generally relates to a composition comprising a genetic probe disclosed herein.

In yet another aspect, the invention generally relates to a composition comprising a PCa cell infected with a genetic probe disclosed herein.

In yet another aspect, the invention generally relates to a method for increasing TfR level on a PCa cell surface, comprising infecting a PCa cell with a genetic probe capable of specific upregulation of TfR expression level in the infected PCa cell without upregulation of TfR expression level in infected nonmalignant prostate cells.

In yet another aspect, the invention generally relates to a method for detecting the presence of a PCa cell. The method comprises: infecting a cell with a genetic probe, wherein the genetic probe is capable of specific upregulation of transferrin receptor (TfR) expression level in an infected PCa cell without upregulation of TfR expression level in an infected nonmalignant prostate cell; and measuring (e.g., detecting and/or analyzing) the surface TfR level on the infected prostate cell to determine whether the prostate cell is malignant or nonmalignant.

In yet another aspect, the invention generally relates to a method for diagnosing prostate cancer in a subject. The method comprises: administering to the subject a genetic probe disclosed herein thereby causing an increase in a surface TfR level on PCa cells without causing an increase in a surface TfR level on nonmalignant prostate cells; and measuring (e.g., detecting and/or analyzing) the surface TfR level on prostate cell surfaces to determine whether the subject suffers from prostate cancer.

In yet another aspect, the invention generally relates to a genetic probe capable of specific upregulation of transferrin receptor (TfR) expression level in a malignant cell of a cell type infected with the genetic probe, wherein the genetic probe does not upregulate TfR expression level in a non-malignant cell of the cell type.

In yet another aspect, the invention generally relates to a genetic probe capable of specific upregulation of human epidermal growth factor receptor 2 (HER2) receptor expression level in a malignant cell of a cell type infected with the genetic probe, wherein the genetic probe does not upregulate HER2 receptor expression level in a nonmalignant cell of the cell type.

In yet another aspect, the invention generally relates to a method for treating PCa. The method comprises administering to a subject in need thereof of a genetic probe disclosed herein thereby causing an increase in a surface TfR level on PCa cells without causing an increase in a surface TfR level on nonmalignant prostate cells; and administering to the subject an anticancer agent that targets TfR.

In yet another aspect, the invention generally relates to a method for treating PCa. The method comprises administering to a subject in need thereof of a genetic probe capable of specific upregulation of HER2 receptor expression level in an infected malignant PCa cell, wherein the genetic probe does not upregulate HER2 receptor expression level in a nonmalignant prostate cell; and administering to the subject an anticancer agent that targets HER2 receptor.

BRIEF DESCRIPTION OF THE DRAWINGS

FIG. 1. A schematic illustration of the synergistic gene-nano strategy utilized to enhance the Tf-conjugated nanoparticle tumor-homing in PCa. Due to the unique tissue-specificity of the DD3 promoter for PCa, the constructed gene probe, namely $P_{DD3}$-TfR-WPRE-$P_{CMV}$-Luc, significantly upregulates the expression of TfR and Luc only in the PCa cells (A). As a result, the elevated TfR proteins on the tumor cells mediated by the genetic probes could significantly enhance the tumor-targeting ability and simultaneously minimize the off-targeting of Tf-conjugated nanoprobes (B).

FIG. 2. Characterization of $P_{DD3}$-TfR-WPRE-$P_{CMV}$-Luc. (A) A schematic diagram of the constructed gene probe, in which the expression of the TfR gene was regulated by the PCa-specific DD3 promoter and the WPRE enhancer. The expression cassette of Luc, as driven by the DD3 and CMV promoter together, was inserted downstream of the TfR gene to non-invasively visualize the TfR expression. (B) The structure of the constructed gene probes verified by PCR using sets of primers corresponding to several important regions of the generated virus. The relative expression of the TfR gene measured by Western blot analysis in 293T cells (C), C42 cells (D), LNCaP cells (E), and T24 cells (F) after infection with Ad.$P_{DD3}$-TfR-WPRE-$P_{CMV}$-Luc (Ad.DD3) or Ad.Null (a negative control). β-actin was used as the internal control.

FIG. 3. (A) Tumor-targeted bioluminescence imaging of LNCaP tumor-bearing mice after injection of Ad.DD3 demonstrate the specific expression pattern of the constructed Ad.DD3 in prostate tissue. The IHC staining of TfR expression at 7 days after the mice were treated with Ad.DD3 (B) or PBS (C), shows that Ad.DD3-treated tumors expressed significantly higher TfR than the PBS-treated tumors.

FIG. 4. Characterization of Tf-USPIONs. (A) HRTEM images of Tf-USPIONs. Scale bar: 20 nm. In vitro T2-weighted MR images (B) and their signal intensity (C) of LNCaP cells after incubation with Tf-USPIONs, USPIONs and PBS, respectively. T2-weighted MR images of Tf-USPIONs solution (D) and their signal intensity (E) at the Fe concentrations of 0, 0.01, 0.02, 0.05, 0.1 and 0.2 mM, respectively. (F) A linear fitting of 1/T2 with respect to Fe concentrations, indicating the T2 relaxivity value of the prepared nanoprobes was 85.33 $mM^{-1}S^{-1}$. ***P<0.0001 for Tf-USPIONs versus USPIONs and PBS.

FIG. 5. (A) T2 weighted MR imaging of tumor-bearing mice before and after the treatment of Ad.DD3+Tf-USPIONs or single Tf-USPIONs. (B) The coronal T2 weighted images of Ad.DD3-infected tumors after the injection of Tf-USPIONs and their bioluminescent images prior to MR imaging. (C) The statistical analysis of the T2 signal intensity of tumors before and after being treated with Ad.DD3+Tf-USPIONs or Tf-USPIONs using Student's t test. Note: *p<0.05, and **p<0.005. (D) T2-weighted MR images and their pseudo-color images at 4 h post-injection of Tf-USPIONs into the Ad.DD3-infected or un-infected tumors.

FIG. 6. Images of H&E-stained sections of tumors and normal organs from different treatment groups. No histological changes were visualized in the tumor, liver, spleen, kidney, brain, heart, or lung at 2 weeks after treatment with PBS, Ad.DD3, Ad.DD3+Tf-USPIONs or PBS+Tf-USPIONs stained sections demonstrated the good in vivo biosafety of the combined application of Ad.DD3 with Tf-USPIONs. The magnifications were 40×.

FIG. 7. A schematic diagram of the adenoviral shuttle vector pHBAd-U6-GFP that was used for the construction of Ad.DD3.

FIG. 8. Schematic diagrams of Ad.Null (A), Ad.Luc (B) and Ad.DD3 (C). Ad.Null and Ad.Luc were received from Hanbio (Shanghai) Biotechnology Co., Ltd and used as control. Ad.Null is an empty adenovirus under the constitute CMV promoter. That's to say, no expression cassettes like Luc and TfR gene were inserted into the downstream of the CMV promoter in Ad.Null. Ad.Luc can express the Luc gene under the constitute CMV promoter in both PCa tumors and non-Pca tissues.

FIG. 9. A western blot analysis of TfR expression in LNCaP cells 24 hours after being infected with Ad.Null, Ad. Luc, and Ad.DD3. GAPDH was set as the internal reference.

FIG. 10. The prone and supine bioluminescence imaging of the LNCaP xenograft tumor-bearing nude mice after being infected with Ad.DD3. The bioluminescence signal derived from the Luc reporter of Ad.DD3 was only visualized in tumor regions, which non-invasively demonstrates the specific-targeted expression pattern of Ad.DD3 in vivo.

FIG. 11. The bioluminescence imaging of LNCaP xenograft tumor-bearing nude mice after the treatment of Ad.Luc. The bioluminescent signal was observed in the tumors and their surrounding tissues. Meanwhile, the bioluminescent range enlarged over time, with no correlation to tumor sizes.

FIG. 12. The immunostaining analysis of TfR expression in different normal organs after the LNCaP xenograft tumor-bearing nude mice were treated with Ad.DD3. No obvious Tf expression was observed in the normal tissues, including the liver, kidney, spleen, lung, brain and prostate. Compared with the remarkably elevated expression of TfR that was detected in the Ad.DD3-infected tumor tissues, this immunostaining analysis confirmed the tumor-specific function of Ad.DD3 to upregulate TfR expression in prostate cancer. Magnifications, 20×.

FIG. 13. TEM image of the USPIONs at different scale bars [(A) 200 nm, (B)100 nm, and (C)50 nm], and their size distribution (D). The as-prepared USPIONs were spherical, monodisperse and uniform, with an average size of approximately 6 nm.

FIG. 14. FTIR spectra of Tf-USPIONs, demonstrating the successful conjugation of Tf and USPIONs. The spectrum for carboxylated USPIONs showed two peaks at 1550 and 1405 $cm^{-1}$, which were attributed to the antisymmetrical vibration and symmetric vibration of the COO— groups respectively. However, these peaks redshifted and weakened, while two new peaks at 1630 and 1565 $cm^{-1}$ representing characteristically stretching of vibrations of amide bonds. This result indicated successfully construction of the coupling between the Tf and the carboxylated USPIONs.

FIG. 15. A photograph of the stock solution (A) and its diluted sample during a 2 week storage period. After freeze-drying, the lyophilized Tf-USPIONs could be easily redissolved in PBS in order to obtain different concentrations of Tf-USPIONs solutions. After being stored at room temperature for 2 months, no precipitation was found in these uniformly dark solutions, demonstrating the good colloidal stability and dispersity of the Tf-USPIONs nanoprobes.

FIG. 16. X-ray powder diffraction (XRD) pattern of the prepared Tf-USPIONs. The diffraction peaks appeared at the Bragg angles 2θ~30.38°, 35.48°, 43.09°, 53.52°, 57.14°, and 62.68°. According to JCPDS card no. 19-0629, all the diffraction peaks could be indexed to face-centered cubic phase of $Fe_3O_4$.

FIG. 17. The magnetic hysteresis loop curves of the prepared Tf-USPIONs nanoprobes, demonstrating the superparamagnetic property of Tf-USPIONs nanoprobes at room temperature.

FIG. 18. The MTT cell viability assay under different concentrations of Tf-USPIONs. The results revealed that cell growth was not inhibited by the treatment with Tf-USPIONs, demonstrating the negligible cytotoxicity of the prepared nanoparticles.

FIG. 19. In vivo MR images of the un-infected LNCaP tumor-bearing mice after intravenous injection of 200 μL Tf-USPIONs (0.5 mg/mL). The arrows indicate the tumor regions.

FIG. 20. (A) The T2 signal intensity of tumors before and at 0.5 h, 2 h, 4 h after the treatment of Ad.DD3+Tf-USPIONs. The mice treated with PBS+Tf-USPION were used as control. (B) The statistical analysis of the T2 signal intensity of tumors before and after being treated with Ad.DD3+Tf-USPIONs or PBS+Tf-USPIONs using Student's t test. Note: *$p<0.05$, and **$p<0.005$. (C) The average change in the T2 signal intensity of tumors normalized by its baseline level. After treatment with Tf-USPIONs, the Ad.DD3-infected tumors showed more rapid and dramatic T2 signal change than the PBS-treated group.

FIG. 21. In vivo MR images of the Ad.DD3-infected LNCaP xenograft tumor-bearing mice after intravenous injection of 200 μL Tf-USPIONs (0.5 mg/mL). The arrows indicate the tumor regions. Transverse T2-weighted MR image at 4 h post-injection of Tf-USPIONs showed a definite boundary between the hypo-intensive tumor mass and its surrounding tissues.

FIG. 22. In vivo T2 weighted MR images of the liver of the Ad.DD3-infected LNCaP xenograft tumor-bearing mice before and after injection of 200 μL Tf-USPIONs (0.5 mg/mL). The mice treated with pure Tf-USPIONs were used as control.

FIG. 23. In vivo T2 weighted MR images of the kidney of the Ad.DD3-infected LNCaP xenograft tumor-bearing mice before and after injection of 200 μL Tf-USPIONs (0.5 mg/mL). The mice treated with pure Tf-USPIONs were used as control.

FIG. 24. The T2 signal intensity of livers (A), kidneys (B), and muscles (C) after the injection of Ad.DD3+Tf-USPIONs or pure Tf-USPIONs, respectively.

FIG. 25. Body weight changes of the LNCaP xenograft tumor-bearing mice before and after treatment of Ad.DD3 and Tf-USPIONs. The mice were pre-treated with Ad.DD3 on the first day. Subsequently, Tf-USPIONs were injected into the Ad.DD3-infected mice on the eighth day. No significant body weight changes were observed during an observation period of 15 days.

FIG. 26. The TGA curves of USPIONs and Tf-USPIONs.

FIG. 27. Changes of tumor volume after different treatment indicated Ad.DD3 enhanced the therapeutic efficacy of Dox in tumor bearing mice.

FIG. 28. Tumor masses excised from the mice at 12 days after treatment with Dox, Ad.DD3+Dox, Tf-Dox, and Ad.DD3+Tf-Dox.

FIG. 29. HE-staining results of tumor-bearing mice after treatment with PBS or Ad.DD3 indicated negligible effect of Ad.DD3 on the histological structure of major organs.

DETAILED DESCRIPTION OF THE INVENTION

The invention is based in part on the discovery of a novel class of genetic probes and bioactive agents useful in cancer diagnosis and treatment. The invention also provides related compositions and methods of use for cancer diagnostic and therapeutic applications.

To address the limitations of existing PCa targeting methods, a new synergetic genetic-nanoparticle tumor homing strategy is developed that significantly amplifies Tf conjugated ultrasmall superparamagnetic nanoparticle PCa tumor homing and its concomitant MR imaging identification. In addition, this strategy assists in the visualization and localization of small PCa lesions and allows for contrast enhancement between ultrasmall PCa lesions (e.g., less than 5 mm) and normal tissues which are otherwise blurred with nanoparticles themselves, thus further addressing an unmet need in MRI imaging for focal therapy.

A key feature of the disclosed approach is based on the unique PCa-specific expression of a differential display code 3 gene (DD3, also known as PCA3), a non-coding RNA which is exclusively expressed in PCa cells. A promoter of the DD3 gene is employed to significantly elevate the levels of TfR on PCa cell in order to enhance Tf-conjugated ultrasmall superparamagnetic nanoparticle PCa homing and MRI imaging contrast. As one of the most PCa-specific biomarkers, DD3 has been used as a clinical characteristic signature for the early screening, patient follow-up check-ups, prognosis prediction, and gene therapy of PCa. (Verhaegh, et al. 2000 *J. Biol. Chem.* 275, 37496; Kok, et al. 2002 *Cancer Res.* 62, 2695; Schalken, et al. 2003 *Urology* 62, 34; Fan, et al. 2010 *Int. J. Cancer* 127, 707; Ding, et al. 2012 *Plos One* 7, e35153; Neveu, et al. 2016 *Oncotarget.* 7, 1300.)

In one aspect, the invention generally relates to a genetic probe for specific upregulation of TfR expression level in an infected PCa cell without upregulating TfR expression level in a nonmalignant prostate cell, wherein the genetic probe comprises a promoter of DD3 gene and TfR gene and upregulation of TfR expression level results in an increase of TfR level on the PCa cell's surface.

In certain embodiments, the genetic probe further comprises a woodchuck hepatitis virus post-transcriptional regulatory element (WPRE) sequence.

In certain embodiments, the genetic probe comprises a viral vector. Any suitable viral vector may be employed. In certain embodiments, the viral vector is selected from the group consisting of adenovirus vector, adeno-associated viruses (AAV), alphaviruses, flaviviruses, herpes simplex viruses (HSV), measles viruses, rhabdoviruses, retroviruses, lentiviruses, Newcastle disease virus (NDV), poxviruses, and picornaviruses. In certain embodiments, non-virus cargos are used as the vectors of the genetic probes, for example, inorganic nanoparticles, cationic lipid- and polymer-based systems.

In certain embodiments, the genetic probe comprises $P_{DD3}$-TfR-WPRE-$P_{CMV}$.

In certain embodiments, the genetic probe further comprises the Luc gene.

In another aspect, the invention generally relates to a PCa cell infected with a genetic probe disclosed herein.

In yet another aspect, the invention generally relates to a composition comprising a genetic probe disclosed herein.

In yet another aspect, the invention generally relates to a composition comprising a PCa cell infected with a genetic probe disclosed herein.

In yet another aspect, the invention generally relates to a method for increasing TfR level on a PCa cell surface, comprising infecting a PCa cell with a genetic probe capable of specific upregulation of TfR expression level in the infected PCa cell without upregulation of TfR expression level in infected nonmalignant prostate cells.

In certain embodiments of the method, the genetic probe comprises a promoter of DD3 gene and TfR gene.

In certain embodiments of the method, the genetic probe further comprises a WPRE sequence.

In certain embodiments of the method, the genetic probe comprises a viral vector. Any suitable viral vector may be employed. In certain embodiments, the viral vector is selected from the group consisting of adenovirus vector, AAV, alphaviruses, flaviviruses, HSV, measles viruses, rhabdoviruses, retroviruses, lentiviruses, NDV, poxviruses, and picornaviruses. In certain embodiments, non-virus cargos are used as the vectors of the genetic probes, for example, inorganic nanoparticles, cationic lipid- and polymer-based systems.

The TfR level on the surface an infected PCa cell may be increased from about 10% to about 40% (e.g., about 20% to about 40%, about 25% to about 40%, about 10% to about 30%, about 10% to about 25%) compared to non-infected PCa cell.

In yet another aspect, the invention generally relates to a method for detecting the presence of a PCa cell. The method comprises: infecting a cell with a genetic probe, wherein the genetic probe is capable of specific upregulation of transferrin receptor (TfR) expression level in an infected PCa cell without upregulation of TfR expression level in an infected nonmalignant prostate cell; and measuring (e.g., detecting and/or analyzing) the surface TfR level on the infected prostate cell to determine whether the prostate cell is malignant or nonmalignant.

In certain embodiments of the method, the genetic probe comprises a promoter of DD3 gene and TfR gene.

In certain embodiments of the method, the genetic probe further comprises a viral vector. Any suitable viral vector may be employed. In certain embodiments, the viral vector is selected from the group consisting of adenovirus vector, AAV, alphaviruses, flaviviruses, HSV, measles viruses, rhabdoviruses, retroviruses, lentiviruses, NDV, poxviruses, and picornaviruses. In certain embodiments, non-virus cargos are used as the vectors of the genetic probes, for example, inorganic nanoparticles, cationic lipid- and polymer-based systems.

In certain embodiments of the method, the genetic probe further comprises a WPRE sequence.

In certain embodiments of the method, the genetic probe comprises $P_{DD3}$-TfR-WPRE-$P_{CMV}$.

In certain embodiments of the method, the genetic probe further comprises the Luc gene.

In certain embodiments, the method further comprises contacting the infected prostate cell with a Tf-labeled contrast agent.

In certain embodiments, the Tf-labeled contrast agent is a Tf-conjugated ultra-small superparamagnetic iron oxide nanoparticle.

In yet another aspect, the invention generally relates to a method for diagnosing prostate cancer in a subject. The method comprises: administering to the subject a genetic probe disclosed herein thereby causing an increase in a surface TfR level on PCa cells without causing an increase in a surface TfR level on nonmalignant prostate cells; and measuring (e.g., detecting and/or analyzing) the surface TfR level on prostate cell surfaces to determine whether the subject suffers from prostate cancer.

In certain embodiments of the method, the genetic probe comprises a promoter of DD3 gene and TfR gene.

In certain embodiments of the method, the genetic probe further comprises a viral vector. Any suitable viral vector may be employed. In certain embodiments, the viral vector is selected from the group consisting of adenovirus vector, AAV, alphaviruses, flaviviruses, HSV, measles viruses, rhabdoviruses, retroviruses, lentiviruses, NDV, poxviruses, and picornaviruses. In certain embodiments, non-virus cargos are used as the vectors of the genetic probes, for example, inorganic nanoparticles, cationic lipid- and polymer-based systems.

In certain embodiments of the method, the genetic probe further comprises a WPRE sequence.

In certain embodiments of the method, the genetic probe comprises $P_{DD3}$-TfR-WPRE-$P_{CMV}$.

In certain embodiments of the method, the genetic probe further comprises the Luc gene.

In certain embodiments, the method further comprises contacting the infected prostate cell with a Tf-labeled contrast agent.

In certain embodiments of the method, the Tf-labeled contrast agent is a Tf-conjugated ultra-small superparamagnetic iron oxide nanoparticles (Tf-USPIONs).

In certain embodiments, the method further comprises measuring a size of a PCa lesion.

In certain embodiments, the size of the PCa lesion is between about 1 mm and about 5 mm (e.g., about 1 mm and about 4 mm, about 1 mm and about 3 mm, less than about 4 mm, less than about 3 mm).

In yet another aspect, the invention generally relates to a genetic probe capable of specific upregulation of transferrin receptor (TfR) expression level in a malignant cell of a cell type infected with the genetic probe, wherein the genetic probe does not upregulate TfR expression level in a nonmalignant cell of the cell type.

In certain embodiments, the malignant cell is a prostate cancer cell.

In certain embodiments, the malignant cell is a breast cancer cell.

The invention can be applied to various cell types. In certain embodiments the malignant cell is a prostate cancer cell. In certain embodiments the malignant cell is a breast cancer cell.

In yet another aspect, the invention generally relates to a genetic probe capable of specific upregulation of human epidermal growth factor receptor 2 (HER2) receptor expression level in a malignant cell of a cell type infected with the genetic probe, wherein the genetic probe does not upregulate HER2 receptor expression level in a nonmalignant cell of the cell type.

In certain embodiments, the malignant cell is a prostate cancer cell.

In certain embodiments, the malignant cell is a breast cancer cell.

In yet another aspect, the invention generally relates to a method for treating PCa. The method comprises administering to a subject in need thereof of a genetic probe disclosed herein thereby causing an increase in a surface TfR level on PCa cells without causing an increase in a surface TfR level on nonmalignant prostate cells; and administering to the subject an anticancer agent that targets TfR.

Any suitable anticancer agent that targets TfR may be utilized, for example, a Tf-labeled cytotoxic agent. In certain embodiments, the anticancer agent is selected from transferrin immunotoxin Tf-CRM107 (TransMid®, Weaver et al. 2003 *J. Neurooncol* 65 (1) 3-13; Laske, et al. 1997 *Nat. Med.* 3 (12) 1362-1368), MBP-426 (Mebiopharm, Tf-PEG lipoplex, NCT00355888, clinicaltrials.gov; NCT00964080, clinicaltrials.gov), SGT-53 (SynerGene Therapeutics, Tf-Cationic lipid complex, NCT00470613, clinicaltrials.gov), SGT-94 (SynerGene Therapeutics, Tf-Cationic lipid complex, NCT01517464, clinicaltrials.gov), CALAA-01 (Tf-conjugated Calandro Pharmaceuticals, Polymeric nanoparticle, NCT00689065, clinicaltrials.gov), Tf-ricin A chain (RTA) conjugates (Raso V, et al. 1984 *J Biol Chem.* 259: 1143-1149), Tf-saporin conjugates (Bergamaschi, et al. 1988 *Br J Haematol.* 68:379-384; Ippoliti, et al. 1995 *Faseb J.* 9:1220-1225), Tf-Doxorubicin/Adriamycin® conjugates (Singh, et al. 1998 *Anticancer Res.* May-June, 18(3A):1423-7; Kratz, et al. 1998 *J Pharm Sci. March,* 87(3):338-46), the complex MPTC-63 produced by the chemical conjugation of Cisplatin to Tf (Elliott, et al. 1988 *Cancer Detect Prev.* 12(1-6):469-80.), Tf-RNases (Rybak, et al. 1993 *Drug Delivery* 1:3-10).

In yet another aspect, the invention generally relates to a method for treating PCa. The method comprises administering to a subject in need thereof of a genetic probe capable of specific upregulation of HER2 receptor expression level in an infected malignant PCa cell, wherein the genetic probe does not upregulate HER2 receptor expression level in a nonmalignant prostate cell; and administering to the subject an anticancer agent that targets HER2 receptor.

Any suitable anticancer agent that targets HER2 receptor may be utilized, for example, Trastuzumab (Herceptin), Pertuzumab (Perjeta), Ado-trastuzumab emtansine (Kadcyla, also known as TDM-1), Lapatinib (Tykerb), Neratinib (Nerlynx).

In summary, the invention discloses an unconventional genetic probing strategy that uniquely drives and amplifies TfR expression in PCa tumor cells specifically, thereby improving the efficiency of the Tf-TfR based nanoparticle tumor-homing and promoting the targeting accumulation of Tf-based nanoprobes in PCa cells. The dramatically increased accumulation of Tf-USPIONs in PCa lead to superior MRI contrast enhancement relative to surrounding normal tissues, allowing for a highly sensitive and precise early detection of ultra-small PCa lesions. The ultrasmall-sized and hypointensive lesion (e.g., –4 mm or smaller) is able to be clearly distinguished in T2WI in a short time post-injection of MRI contrast agents. Such rapid and ultra-small PCa lesion MRI detection is particularly clinically important because the success of focal PCa therapy ideally requires that the actual size of the PCa lesion be smaller than 5 mm or that a single PCa lesion on MRI is less than 12 mm. Using this novel strategy, cancer destruction can be maximized and damage to surrounding healthy parenchyma can be minimized, thus achieving a favorable morbidity profile with maximum preserved physiologic functions of the male PCa patients. In addition, since DD3 genes have been demonstrated to be overexpressed in more than 95% of both primary and metastatic PCa, this synergetic genetic-nanoparticle strategy are promising to visualize both local PCa as well as small PCa metastasis like extracapsular extension, adjacent invasion as well as distant metastasis into the bones in the future. In this regard, the invention promises more accurate determination of disease extension at early on and allows the patient the option of a localized therapy.

Moreover, such a genetic probe may also be extended to MRI specific imaging of other types of cancers by using their respective tumor specific promoters, such as the alpha-feto-proteingene promoter for hepatocellular carcinoma (a) Saukkonen, et al. 2004 *Expert Opin. Boil. Ther.* 4, 683; (b) Kanai, et al. 1996 *Hepatology* 23, 1359; (c) Willhauck, et al., 2008 *Gene Therapy* 15, 214), G250 promoter for renal carcinoma (a) Liu, et al. 2012 *Cancer Science* 103, 1880; (b) Grabmaier, et al. 2004 *Oncogene* 23, 5624; (c) Saukkonen, et al. 2004 *Expert Opin. Boil. Ther.* 4, 683), the erb2 promoter for breast cancer (a) Cordo, et al. 2015 *Oncogene* 34, 3413; (b) Wang, et al. 2001 *Semin. Oncol.* 28, 21; (c) Saukkonen, et al. 2004 *Expert Opin. Boil. Ther.* 4, 683), carcinoembryonic antigen promoter for colorectal cancer (Kerr 2003 *Nat. Rev. Cancer* 3, 615; (c) Saukkonen, et al. 2004 *Expert Opin. Boil. Ther.* 4, 683). Instead of the TfR, other downstream functional genes, such as PTEN (Ding, et al. 2012 *PLOS ONE* 7, e35153) and P53 (Tazawa, et al.

*Expert Opin. Boil. Ther.* 2013, 13, 1569; Liu, et al. 2011 *Mol. Oncol.* 5, 545), can also be conveniently introduced into any cassette in the genetic probe, thus realizing multimodal theranostic applications. The novel genetic amplified nanoparticle tumor homing strategy disclosed herein provides a new foundation for early tumor MRI detection and subsequent treatment that are otherwise limited by existing MRI imaging probes.

EXAMPLES

A PCa cell specific genetic probe $P_{DD3}$-TfR-WPRE-$P_{CMV}$-Luc was designed, prepared and tested. A key to this genetic probe was the use of a promoter of the DD3 gene, which was introduced into the genetic probe in order to achieve the exclusive expression of the nanoparticle targeting receptor (i.e., TfR) gene together with the downstream luminescence reporter Luc gene in PCa cells. In order to boost the expression levels of the genetic probe, the woodchuck hepatitis virus post-transcriptional regulatory element (WPRE) was placed in the genetic probe. WPRE was reportedly able to induce a 4 to 9-fold increase in downstream gene expression. (Zufferey, et al. 1999 *J. Virol.* 73, 2886; Loeb, et al. 1999 *Hum. Gene. Ther.* 10, 2295.)

This genetic probe exhibited precise and specific expression with respect to the downstream functional genes (e.g., TfR and Luc gene) in PCa by the regulation of the PCa-specific promoter as well as the enhancer (FIG. 1A).

When coupled with transferrin conjugated ultra-small iron oxide superparamagnetic nanoprobes (i.e., Tf-US-PIONs), the MRI findings confirmed that the genetic probes can significantly enhance the tumor-targeting ability of Tf-based nanoprobes for early tumor detection, as compared to Tf-USPIONs alone (FIG. 1B). This suggests that the genetic strategy offers a new opportunity to efficiently improve the diagnostic effect. The enhanced tumor-specific MR imaging of PCa by the genetic-nano strategy offers highly accurate information regarding the exact tumor location, size, shape, and its relationship with surrounding tissues to support formal recommendations for surgery and the use of focal therapy. This is the first time that genetic approaches have been implemented to amplify the tumor targeting for MR imaging.

The genetic probe $P_{DD3}$-TfR-WPRE-$P_{CMV}$-Luc was constructed by inserting the gene fragments (DD3 promoter, TfR gene, WPRE, CMV promoter, and Luc reporter gene) into the pHBAd-U6-GFP plasmid (FIG. 7). A gene recombination was sequentially performed in order to generate the shuttle vector pAdeasy-$P_{DD3}$-TfR-WPRE-$P_{CMV}$-Luc. The prepared shuttle vector was then successfully packaged into the adenovirus vector. The resulting Ad.$P_{DD3}$-TfR-WPRE-$P_{CMV}$-Luc, namely Ad.DD3 (FIG. 2A), was confirmed via a polymerase chain reaction (PCR). In particular, as can be seen in FIG. 2B, the PCR fragments that were obtained show 3 bright bands at 230 bp, 590 bp, and 2300 bp which are corresponding to the predicted sizes of the DD3 promoter, the WPRE sequence, and the TfR gene respectively. The ability of Ad.DD3 to drive the expression of the TfR gene in the PCa cells was then further demonstrated by Western-blotting assays after the LNCaP cells were infected with Ad.DD3, with Ad.Null (an empty adenovirus under the CMV promoter, no expression cassettes, as shown in FIG. 8A) and Ad.$P_{CMV}$-Luc (namely Ad.Luc, which can express the Luc gene under the CMV promoter in both PCa tumors and non-PCa tissues, as shown in FIG. 8B), used as the control. As a result, Ad.DD3 induced significantly more TfR expression in tumor cells than the control groups (FIG. 9).

Subsequently, the tissue-specific expression pattern of the constructed Ad.DD3 was evaluated in several different cell lines, including PCa cell lines (LNCaP and C42), a non-cancer cell line (293T) with known low TfR expression, and a non-PCa cancer cell line (the bladder cancer T24 cells) with known high TfR expression. As shown in FIG. 2C, the treatment with either Ad.DD3 or Ad.Null, TfR expression increase cannot be observed in 293T cells. Moreover, among the three types of cancer cells that were treated with Ad.DD3, a higher level of TfR protein expression was only observed in the two PCa cells (LNCaP, C42, especially in the LNCaP cells, FIGS. 2D and 2E) than in the Ad.Null-treated samples. In contrast, the Ad.DD3 treated T24 bladder cancer cell does not show noticeable TfR expression increase when compared to Ad.Null treated samples (FIG. 2F). The above results suggest the cell line specificity of Ad.DD3 to PCa in regard to amplifying downstream functional gene (e.g., TfR) expression.

Local administration has been a regular procedure for PCa biopsy, excision and focal therapy. Following this standard procedure, Ad.DD3 was directly injected into PCa (LNCaP) lesions in tumor bearing mice. To evaluate the resulting expression of TfR in vivo, bioluminescence imaging was performed after intratumor injections. The bioluminescent signal derived from Ad.DD3 was clearly visualized in PCa tumor areas at 24 h post-administration, making it readily distinguishable from surrounding tissue (FIG. 3A). The tumor was further monitored by bioluminescence imaging for about 2 weeks. The results showed that the bioluminescence intensity progressively increased over time and the area of luminescence detected increased along with the tumor-growth. Due to the strict PCa cell specificity of Ad. DD3, no detectable bioluminescence was found in the rest of the body (FIGS. 3A and 10). In contrast, the intratumor injection of Ad.Luc in the control experiment led to obvious bioluminescence in the tumors and their surrounding tissues, the range of which enlarged and had no correlation with the tumor sizes (FIG. 11). Notably, the above bioluminescence findings demonstrated that the utilization of the genetic probe Ad.DD3 was an efficient and tumor highly specific method with favorable features with respect to early diagnosis, immediate treatment and timely monitoring before and after treatment.

Besides, the in vivo enhancement effect of the genetic probe Ad.DD3 on TfR expression were further confirmed by the immunohistochemical (IHC) staining with anti-TfR at 7 day post-infection. As a result, Ad.DD3-treated tumors expressed significantly higher TfR than the PBS-treated tumors (FIGS. 3B and 3C). Meanwhile, no obvious immunoreactivity was observed in the normal tissue of the liver, kidney, spleen, lung or brain (FIG. 12), in either the Ad.DD3 or the PBS group. Thus IHC staining further confirmed the strict PCa tumor site overexpression of TfR by AD.dd3, which is in line with results of bioluminescence imaging.

Next, the MRI imaging enhancement effect of the genetic probes was explored with Tf conjugated ultra-small superparamagnetic iron oxide nanoparticles (Tf-USPIONs). USPIONs have been widely used in T2-weighted MRI because of their numerous merits, including ultrasmall particle dimension, high colloidal stability, excellent magnetic properties and outstanding biocompatibility. (Winter, et a. 2018 *Eur. Urol.* 73, 813; Pan, et al. 2012 *Chem. Soc. Rev.* 41, 2912; Jafari, et al. 2015 *Nanotechnology* 26, 75101; Zhou, et al. 2018 *Curr. Opin. Chem. Biol.* 45, 131; Yang, et al. 2018 *J. Am. Chem. Soc.* 140, 4666.)

Moreover, they exhibit large surface area and are facilely functionalized with targeting ligands such as Tf. To prepare Tf-USPIONs, the carboxylated USPIONs with an average diameter of ~6 nm (FIG. 4A and FIG. 13) was synthesized via a reported one-step solvothermal method. (Xuan, et al. 2009 *Chem. Mater* 21, 5079.)

Subsequently, Tf proteins were added into the prepared USPIONs solution and conjugated with USPIONs using EDC/NHS reaction. After vigorous stirring for 16 h, the resulting solution was washed with ultrapure water five times to remove the unreacted Tf. The coupling of the carboxyl groups of USPIONs with Tf was confirmed by FTIR spectra (FIG. 14). Further characterizations showed that each Tf-USPIONs contained ~1.2 Tf. Then, in vitro MR imaging experiments with the same Fe concentrations of both Tf-USPIONs and USPIONs were performed with the PC-3 cells, and PBS. The quantitative analysis of MR signal intensities showed that the cells ($2\times10^6$ cells in 1 mL PBS) treated with Tf-USPIONs nanoparticles displayed significantly darker signals compared with those (the same concentration of cells) treated with USPIONs and PBS (FIGS. 4B and 4C), indicating that USPIONs can be more efficiently internalized by tumor cells after the functional modification with Tf.

The resultant Tf-USPIONs possessed excellent physical and chemical characteristics, including an ultrasmall hydrodynamic size of about 11 nm, good colloidal stability (FIG. 15), and a remarkable T2 enhancement effect (FIGS. 4D and 4E) with high transverse relaxivity of 85.33 $mM^{-1}$ $s^{-1}$ (FIG. 4F). Meanwhile, MTT results revealed that the cell growths were not inhibited by the treatment of Tf-USPIONs (FIG. 18), indicating the negligible cytotoxicity of the prepared nanoparticles.

One week after the pre-treatment of the Ad.DD3, Tf-USPIONs at a dose of 5 mg Fe/kg body weight were intravenously injected into the LNCaP tumor-bearing mice via the tail veins (FIG. 5A). In order to confirm the successful TfR expression of Ad.DD3 in tumor areas, the tumor bearing mice were imaged by bioluminescence imaging 12 h before MR imaging. The result showed strong bioluminescence in left shoulder, with approximately 1 cm in size from bioluminescence, indicating the successful pre-treatment of Ad.DD3 (FIG. 5B). Another group of mice was pre-injected with PBS and administered the same dose of Tf-USPIONs solutions as the control. At the baseline, the tumor areas in the two groups, located in the left shoulder, exhibited heterogeneously high-mixed intensity on the T2WI (FIG. 5A). After injection of Tf-USPIONs, the signal intensity in the PBS-treated tumors fell slowly during the 4 h observation period, with a vague boundary on T2-weighted MRI (FIG. 19). This result revealed the MR detection efficacy of tumor using Tf-USPIONs was suboptimal. Conversely, a remarkably rapid negative T2WI enhancement effect was observed in the Ad.DD3-treated tumors at 0.5 h post-injection of Tf-USPIONs (FIGS. 5C and 20A). At this time, quantification from tumor imaging (FIG. 20B) showed the Ad.DD3-treated tumors exhibited a 33% T2 signal change, which is over 3.6 times the relative signal changes of the PBS-treated group (about 9%). This remarkable contrast enhancement clearly outlined the boundary of tumor masses at 4 h, thus making the ultrasmall tumor lesions (~4 mm diameter from MRI imaging) distinguishable from the surrounding tissue (FIGS. 5D and 21). The fast-acting time for contrast enhancement (less than 0.5 h) and long observation duration (over 3.5 h) of the synergetic genetic-nanoparticle strategy are particularly important from the standpoint of clinic practice. Taken together, the above results indicated that the constructed Ad.DD3 gene probe could enhance the targeting abilities of the nanoprobes by specifically amplifying the expression of a receptor protein on tumor cells, and thereby achieve a more rapid, high-resolution and clear T2WI enhanced MR imaging than using traditional Tf-USPIONs only.

The above imaging experiments clearly showed a significantly rapid decrease in the T2 signal and much clearer tumor boundary of the Ad.DD3-infected tumors when compared to that of PBS treated groups (FIG. 5). To further explore the effect of the Ad.DD3 on the TfR expression in normal tissues, the T2 signal intensities of the liver, kidney and muscle were compared between the Ad.DD3 and PBS groups (FIGS. 22-24). As a result, no noticeable difference was found by MRI in normal tissues between the two groups, which is in line with the IHC results of TfR expression in PCa and different normal organs (FIG. 12). Moreover, after the treatment of Ad.DD3 and Tf-USPIONs, no apparent signs of toxic side-effects were also found in the hematoxylin/eosin staining experiments (FIG. 6). In particular, to evaluate the potential toxicity of Ad.DD3 and Tf-USPIONs in vivo, each dissected organ was cut into 5-μm-thick sections. Five sections per organ were randomly selected from left to right. About 20 locations of each organ (3-5 fields per section×5 sections per organ) were analyzed by a pathologist blinded to the experiments. Based on the morphological observation of each field using a fluorescence microscope, no evidence of structural disorders, degeneration, necrosis or inflammatory infiltration was found in these organs in all groups (FIG. 6). Especially, careful observation of the HE-stained sections of livers, the major metabolic organ of adenovirus revealed no pathological changes in their gross morphology or lobular structures. As another metabolic organ of the body, kidneys exhibited no pathological damages in the cortex or medulla. In addition, the mice treated by both Ad.DD3 and Tf-USPIONs showed no significant body weight loss (FIG. 25). All of the above results suggest the side effects of the strategy are negligible.

Besides Tf conjugated contrast agents (like Tf-US-PIONs), the genetic probes can be also used to enhance the tumor homing ability of transferrin modified therapeutic compounds and thus further improve their antitumor efficacy. Here, Tf labeled doxorubicin nanoparticles (i.e., Tf-Dox) were taken as an example. Tf-Dox was prepared as following process: First, 50 mg of Tf protein was dissolved in 5 mL of PBS at 37° C. After complete dissolution, 5 mg of Dox was added under constant stirring. Another 12 hours later, the reaction mixture was concentrated and washed with PBS by using centrifugal ultrafiltration (Millipore, molecular size cutoff of 30 kDa) at 4000 g to remove unreacted Dox. This purification procedure was repeated 3 times. The obtained Tf-Dox nanoparticles were finally dissolved in 4.0 mL of PBS for further experiments.

To study the in vivo enhancement effect of the genetic probes on the antitumor efficacy of Tf-Dox, we first established xenograft models of prostate cancer by subcutaneous injection of LNCap tumor cells (about $1\times10^6$) in Matrigel (BD Biosciences; 1/1) into the left shoulder of BALB/c male mice. After ~2 weeks post-inoculation when tumors grew to ~0.8-1.0 cm in diameter, mice were randomly divided into four groups (n=3/group) and treated with: (1) Dox (22 μg/mL), (2) Ad.DD3+Dox (containing 22 μg/mL of Dox), (3) Tf-Dox (containing 5 g/mL of Dox), (4) Ad.DD3+Tf-Dox (containing 5 μg/ml of Dox), respectively. Ad.DD3 was pre-injected into the tumors 7 days before the intravenous administration of Dox or Tf-Dox. During 14 days of observation, we monitored the tumor volumes according to the following formula: $V=a\times b^2/2$ where a and b were the longest and shortest diameters of the tumor, respectively, measured using a Vernier caliper. As shown in FIGS. 27-28, an increase of tumor volume was visualized in Tf-Dox group owing to the relatively low content of Dox (5 µg/mL). Whereas, Ad.DD3+Tf-Dox showed the most pronounced tumor inhibition effect at the same low Dox concentration, demonstrating that the genetic probes could significantly enhance the antitumor efficacy of Tf-labelled nanoparticles. Notably, the tumor inhibitory caused by Ad.DD3+Tf-Dox (5 µg/ml) was still better than a 4.5-fold concentration of free DOX (22 µg/mL), indicating that the genetic probes can optimize the therapeutic performance of Dox exclusively in tumor regions while minimizing its administration dose. The reduced injection dose, in turn, is promising to lower down the distribution and biotoxicity of drugs towards the normal tissues. Meanwhile, no significant difference was observed in the trends of tumor volume between the Ad.DD3+Dox group and pure Dox group, indicating that the genetic probes alone had no tumor inhibition effect. The non-toxicity of pure Ad.DD3 gene probes towards tumor tissues was further confirmed by the results of hematoxylin and eosin (H&E, FIG. 29) staining assays. Thus, the optimized therapy outcome of the gene-nanoparticle synergetic strategy is resulted from the enhanced tumor homing ability of the nanoparticles leading to higher DOX accumulation in the tumor cells rather than the antitumor effect of the gene probes. Furthermore, no apparent histological changes were observed in the normal organs harvested from pure Ad.DD3-treated mice, similar to that of the PBS-treated group, demonstrating the excellent biocompatibility of the genetic probes which facilitated their further biomedical applications.

Experimental

Construction of Tumor-Specific Gene Vectors Ad.$P_{DD3}$-TR-WPRE-$P_{CMV}$-Luc

The plasmids carrying the minimal DD3 promoter (AF279290 nt309-522) and TfR gene were received from Institute of Medicine and Biotechnology and Third Affiliated Hospital of Zhongshan University, respectively. The pLV-shRNA plasmid harboring WPRE and the adenoviral shuttle vector pHBAd-U6-GFP (FIG. 19) were supplied by Hanbio (Shanghai) Biotechnology Co., Ltd. First, the sequence of the DD3 promoter, TfR fragment and WPRE regulatory element were amplified via PCR reaction with forward and reverse primers that are listed in Table 1. The reaction conditions were as follows: Pre-denaturing at 95° C. for 2 min, followed by 35 cycles of amplifications by denaturing at 94° C. for 20 s, annealing at 55° C. for 30 s, and extension at 72° C. for 30 s. After a final extension at 72° C. for 2 min, DNA sequencing was utilized to analyze the amplified products.

Following sequencing, the obtained fragments were sequentially inserted into the pHBAd-U6-GFP plasmid in order to generate the recombinant shuttle plasmid, namely pHBAd-$P_{DD3}$-TfR-WPRE-$P_{CMV}$-GFP. The GFP expression cassette was then replaced by the luciferase reporter gene, and the new shuttle vector pAdeasy-$P_{DD3}$-TfR-WPRE-$P_{CMV}$-Luc was generated by the homologous recombination of the adenoviral shuttle vector pHBAd-$P_{DD3}$-TfR-WPRE-$P_{CMV}$-GFP and the adenovirus backbone plasmid pBHGIox (delta)E1, 3Cre. After being packaged in HEK-293 cells, the construction of the recombinant adenovirus vehicles at the DNA level was confirmed by PCR using the following program: pre-denaturing at 94° C. for 5 min, followed by 30 cycles of denaturing at 94° C. for 30 s, annealing at 55° C. for 30 s, and extension at 72° C. for 1 min, and a final extension at 72° C. for 10 min. The sequences of the primers used for PCR are described in Table 2. Furthermore, in order to achieve virus identification at the protein level, the expression of Ad.$P_{DD3}$-TfR-WPRE-$P_{CMV}$-Luc (namely Ad.DD3) was determined by Western blot assays for TfR protein.

After authentication procedures, the constructed adenovirus was amplified and purified by double cesium chloride density gradient ultracentrifugation and dialyzed in PBS with 10% glycerol solution. A plaque assay was used to measure the titers of the recombinant adenovirus. Viral aliquots were stored at −80° C. for further use.

TABLE 1

The primer sequences used for the amplification
of gene fragments from plasmid vectors by
PCR methods.

| Gene | Direction | Nucleotide sequence |
|------|-----------|---------------------|
| DD3 Promoter | Forward | ACCTCTAGATTGTCAACATAGTG |
| | Reverse | TCCGAATTCTCCACACAAATCTCCC |
| TfR | Forward | AACGAATTCATGATGGATCAAGC |
| | Reverse | AACGGATCCTTAAAACTCATTGT |
| WPRE | Forward | AACGGATCCAATCAACCTCTGGATT |
| | reverse | TCCACCGGTCAGGCGGGGAGGCG |

TABLE 2

The primer sequences for the oligonucleotide
primers used to confirm the structure of the
prepared Ad.DD3 vector by PCR.

| Gene | Direction | Nucleotide sequence |
|------|-----------|---------------------|
| DD3 Promoter | Forward | TTGTCAACATAGTG |
| | Reverse | TCCACACAAATCTCCC |
| TfR | Forward | ATGATGGATCAAGC |
| | Reverse | TTAAAACTCATTGT |
| WPRE | forward | AATCAACCTCTGGATT |
| | reverse | CAGGCGGGGAGGCG |

Western Blot Analysis

To semi-quantitatively analyze the protein expression of TfR, the normal cell lines (293T), PCa cell lines (LNCaP and C42) and non-PCa cell lines (T24 bladder cancer cells) plated in 24-well dishes were transduced with Ad.DD3 or Ad.Null as control. Within 18 h to 24 h post-infection, the cells were lysed in RIPA buffer (Sigma) before the total protein was extracted from the infected cells. The protein concentrations were measured via a Bio-Rad Protein Assay Kit (Bio-Rad). The protein samples were then electrophoretically separated on a SDS-PAGE gel and transferred to a PVDF membrane. After being blocked by TBST containing 5% nonfat dry milk, the membrane was sequentially incubated with the primary antibody for TfR (1:1,000 dilution; Abcam) for 1 h and the secondary antibody linked with HRP (GE Healthcare) at 4° C. overnight. β-actin was used as the internal control for the total protein levels. Finally, the membrane was washed 3 times with PBST, then treated by ECL Western blot detection reagents (Pierce Biotechnology, Rockford, Illinois, USA) and visualized after exposure to cellophane film.

Tumor Mice Model for Prostate Cancer

Male BALB/c nude mice (8 weeks old) weighing 24.0±0.5 g were purchased from Vital River Laboratories (Beijing, China). In accordance to the guidelines with respect to the ethical use of animals, all mouse care and experimental procedures were performed under specific pathogen-free (SPF) conditions. Single cell suspensions of $5 \times 10^6$ LNCaP cells in Matrigel (BD Biosciences) (1/1) were subcutaneously injected into the left shoulder of each mouse in order to establish prostate cancer xenograft models. Further experiments commenced when tumors reached 5-10 mm in diameter (approximately 2-3 weeks after transplantation).

In Vivo Antitumor Efficacy.

Xenograft models of prostate cancer were established by subcutaneous injection of LNCap tumor cells (about $1 \times 10^6$) in Matrigel (BD Biosciences; 1/1) into the left shoulder of BALB/c male mice. After ~2 weeks post-inoculation when tumors grew to ~0.8-1.0 cm in diameter, mice were randomly divided into four groups (n=3/group): (1) Dox (22 μg/ml), (2) Ad.DD3+Dox (containing 22 μg/ml of Dox), (3) Tf-Dox (containing 5 μg/ml of Dox), (4) Ad.DD3+Tf-Dox (containing 5 μg/ml of Dox). Ad.DD3 were pre-injected into the tumors 7 days before the intravenous administration of Dox or Tf-Dox. Changes in tumor volume and body weight were monitored at several scheduled time-points. The volume of the tumor was calculated according to the following formula: $V=a \times b^2/2$ where a and b were the longest and shortest diameters of tumor, respectively, measured using a Vernier calliper. At the end of experiment, the animals were sacrificed and the tumor masses were excised. Results are shown in FIGS. 27-29.

The In Vivo Bioluminescence Imaging of Ad.DD3

18 LNCaP tumor-bearing mice were randomly separated into 3 groups. When the size of a tumor reached 10 mm³, $1 \times 10^{11}$ pfu of Ad.DD3 was directly injected into the tumor at multiple sites. For the purpose of comparison, the other two groups were treated with an equivalent amount of Ad.Luc and Ad.Null under similar conditions, respectively. Subsequently, bioluminescence imaging was carried out over sequential time points for 14 days. Prior to such imaging, the mice were anesthetized with an intraperitoneal injection of 5% chloral hydrate (7 mL/kg). Following the injection of luciferin (100 μL i.p./mouse), bioluminescence imaging was acquired using an in vivo imaging system (NightOWL, Germany). The exposure time was set at 1 min.

Immunohistochemical Staining

When the intensity of the bioluminescence signals reached the maximum level 1 week post-injection of the adenoviruses Ad $P_{DD3}$-TfR-WPRE-$P_{CMV}$-Luc, the treatment group was sacrificed in order to determine the Tf expression via immune-histochemical experiments. Basic IHC protocols have been previously described. Thus, in brief, the excised tissues, including tumor mass and major organs were fixed in neutral buffered formalin, paraffin embedded and sliced into 5 μm sections. After deparaffinization, hydration and antigen retrieval, endogenous peroxidase and serum were blocked using 3% hydrogen peroxide. The sections were then incubated with the primary antibody for Tf (1:1,000 dilution; Abcam) overnight at 4° C. The antibody was detected via a biotinylated goat anti-rabbit secondary antibody, followed by horseradish peroxidase, before the application of peroxidase substrate 3,3'-diaminobenzidine (DAB). Ultimately, TfR-positive cells appeared to be brown.

Synthesis and Characterization of Tf-Labelled USPIONs

Iron(III) chloride hexahydrate (FeCl₃·6H₂O), 1-ethyl-3-(3-dimethylaminopropyl) carbodiimide (EDC), and N-hydroxysuccinimide (NHS) were all purchased from Aladdin Reagent Co. Ltd (Shanghai, China). Sodium acrylate (CH₂=CHCOONa, Na acrylate), sodium acetate (CH₃COONa, NaOAc), and diethylene glycol (DEG) were obtained from Sigma-Aldrich (St. Louis, MO, U.S.). As previously described, superparamagnetic iron oxide nanoparticles with an average size of 6 nm were synthesized via a one-step solvothermal method. (Xuan, et al. 2009 *Chem. Mater* 21, 5079.) First, 0.54 g FeCl₃·6H₂O, 1.5 g Na acrylate, and 1.5 g NaOAc were dissolved in 20 mL DEG and were continuously stirred in a vigorous manner until the mixture turned into a homogeneous yellow solution. The above solution was then heated at 200° C. using a Teflon-lined stainless-steel autoclave for 10 h. Subsequently, the resultant mixture was naturally cooled to room temperature. With the assistance of an external magnet, the resulting Fe₃O₄ particles were washed with ethanol and deionized water 3 times. After being dried in a vacuum for another 12 h, the black product obtained was weighed and redispersed in 5 mL of PBS for further use.

Because the SPION prepared by the above method inherently contained large amounts of carboxyl groups on its surface, it was able to be directly conjugated to the targeting ligand Tf after activation by NHS and EDC. The obtained SPION solution (5 mg) was diluted to a final volume of 4 mL with PBS, before 2 mg EDC and 2 mg NHS were added, and vigorously stirred for 1 h. Then, 1 mg of Tf in 200 μL of PBS (pH 7.4) was poured into the reaction mixture and stirred vigorously for an additional 16 h. The resultant Tf-SPION was washed 3 times with ultrapure water with the help of a magnet to remove the excess reactants. Finally, the purified product was diluted to a final volume of 30 mL with ultrapure water for further characterization using high resolution transmission electron microscopy (HRTEM), X-ray diffractometer (XRD, FIG. 16), dynamic light scattering (DLS), vibrating sample magnetometer (VSM, FIG. 17), a fourier transform infrared (FT-IR) spectrometer and an MR imaging system (1.2T).

MTT Assays

The cytotoxicity of the prepared nanoprobes was evaluated by the MTT assay. PC-3 cells in the log phase were seeded into a 96-well plate at $5 \times 10^3$ cells per well. Once these cells were 80% confluent, they were treated with RPMI-1640 cell medium containing a large concentration range of Tf-USPIONs solution (0 μg/mL, 10 μg/mL, 20 μg/mL, 50 μg/mL, 100 μg/mL, 200 μg/mL) for 24 h. The MTT stock solution (5 mg/mL) was then added to each well in order to incubate for another 4 h. After the addition of DMSO (150 μL/well, Sigma-Aldrich, St. Louis, MO, USA), the assay plate was allowed to stand in a shaker at a constant temperature (Yiheng Technology, Shanghai, China) for 10 min. Finally, the absorbance of each solution was read on a microplate reader (Thermo, Varioskan Flash) at 570 nm. At each concentration, 6 replicative samples were measured.

In Vitro MR Imaging

Prostate tumor LNCaP cells were incubated on a 6-well plate with Tf-USPIONs conjugates, USPIONs (Tf-USPION and USPION are in the same Fe concentrations (0.1 mg/mL), or PBS alone for 24 h. These cells were then washed with PBS buffer (10 mM, pH 7.4) three times in order to remove the non-specific binding of the prepared probes. After being digested with 0.25% trypsin, the above cells at a count of $2 \times 10^6$ were re-suspended in 1 ml of PBS buffer using a 1.5 mL Eppendorf tube. T₂ MRI of the cell suspensions in each tube was obtained by a 3T Siemens MR system with a 32-channel head coil using the following imaging parameters: TR/TE=6000/96 ms; slice thickness=3.0 mm; FOV=199 mm×199 mm; matrix=384×384.

The T2 signal intensities were examined within the region of interest. All of the respective samples were analyzed in triplicates.

In Vivo MR Imaging

When the tumors grew to a diameter of approximately 5-10 mm in the 6 tumor-bearing mice, intra-tumoral injection of Ad.DD3 ($1\times10^{11}$ pfu dissolved in 200 µL of PBS) was performed. At 1 week post-injection, all of the mice were intravenously injected with 200 µL of Tf-USPIONs at a concentration of 0.5 mg/mL. Prior to MR imaging, the mice were imaged by bioluminescence imaging to confirm successful intratumoral injection of Ad.DD3 into the tumors. The control group was treated with equivalent volumes of normal saline. Subsequently, both groups of mice were positioned into a 3.0 T MR imaging system (Siemens) equipped with a 32-channel head coil. Dynamic MR images using a fat-suppressed T2-weighted spin echo sequence (TR/TE/NEX=6000/96/3; FOV, 20 cm; one slice, 3 mm; in-plane resolution, 240×240 µm) were acquired before, as well as 1, 2 and 4 hours after contrast administration. The signal intensity was measured with respect to the selected areas of tumor tissues, the liver, the kidney, the brain, the muscle and the heart. Time-signal curves of the regions of interest were monitored over time. After MRI, mice were euthanized by cervical dislocation.

In Vivo Toxicity Assay

At 2 week post-injection of the recombinant adenovirus (namely 7 days after the treatment of Tf-USPIONs), all of the mice used in the optic and MR imaging experiments were sacrificed in order to dissect the brain, spleen, kidney and liver. Meanwhile, other BALB/c nude mice undergoing the treatment of single Ad.DD3 or PBS were set as the control group and sacrificed so as to dissect the same organs. The organs were fixed in 4% formalin for 1 week, and then washed in PBS for 30 min. After being embedded in paraffin, the tissues were cut into 5 µm-thick sections, mounted on a glass slide and stained with hematoxylin/eosin for 5 min. Finally, morphological changes were observed by a fluorescence microscope.

Statistical Analysis

The data were presented as the means±standard deviation errors ($\bar{x}\pm s$). Statistical significance was determined using Student's t test and chi-square test. P<0.05 was defined as being statistically significant.

Analysis of the Number of Tfs in Each Tf-USPION

As for the number of Tfs in each NP, further characterizations were performed and the results showed that each NP contains about 1.2 Tf. This was calculated using the following steps:

(i) As determined by HRTEM, the spherical USPIONs, namely $Fe_3O_4$ NPs, had an average size (d) of 6.8 nm. Since the density of $Fe_3O_4(p)$ was 5.18 g/cm³, the weight (m) of each USPION was calculated to be $8.52\times10^{-19}$ g by using as the following formula:

$$r = \frac{d}{2}(r \text{ refered to the radius of the spherical } USPIONs)$$

$$V = \frac{4}{3}\pi r^3 = \frac{4}{3}\pi\cdot\left(\frac{d}{2}\right)^3 = \frac{1}{3}\pi d^3 (V \text{ refered to the volume of the spherical } USPIONs)$$

$$m = pV = \frac{1}{3}p\pi d^3$$

(ii) As determined by thermos-gravimetric analysis (TGA, FIG. 26), the vacuum-dried USPIONs contained 84.17% $Fe_3O_4$(w/w). Thus, the per gram of USPIONs contained 0.8417 g of inorganic $Fe_3O_4$ and 0.1583 g of organic composition on their surface.

(iii) According to the results of TGA, the vacuum-dried Tf-USPIONs contained 72.88% $Fe_3O_4$ (w/w, FIG. 26). Thus, the per gram of NPs contained 0.7288 g of inorganic $Fe_3O_4$, namely the weight of $8.55\times10^{17}$ $Fe_3O_4$NPs; Since the ratio between the organic matter on the surface and the inorganic $Fe_3O_4$ was 0.1881 (0.8417 g: 0.1583 g), the weight of organic matter on the surface of 0.7288 g $Fe_3O_4$ was 0.1371 g (0.7288 g multiplied by 0.1881).

(iv) As Tf-USPIONs consisted of Tf, USPIONs and the organic composition on the surface of USPIONs, the content of Tf in the prepared NPs equaled the total weight of Tf-USPIONs (1 g) minus the residual weight of USPIONs (0.7288 g) and the weight of organic compositions (0.1371 g), namely 0.1341 g. Since the molecular weight of human Tf is ~78 KD, 0.1341 g of Tf contained $10.35\times10^{17}$ Tf molecules.

Based on the above analysis, each USPION was conjugated with 1.2 Tf ($10.35\times10^{17}$ divided by $8.55\times10^{17}$).

Materials, compositions, and components disclosed herein can be used for, can be used in conjunction with, can be used in preparation for, or are products of the disclosed methods and compositions. It is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compounds or compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed:

1. A genetic probe for specific upregulation of transferrin receptor (TfR) expression level in an infected prostate cancer (PCa) cell without upregulating TfR expression level in a nonmalignant prostate cell, wherein the genetic probe is an adenovirus vector represented by Ad.P$_{DD3}$-TfR-WPRE-P$_{CMV}$-Luc, wherein P$_{DD3}$ represents the promoter of differential display code 3 (DD3) gene, TfR represents TfR gene, and WPRE represents a woodchuck hepatitis virus post-transcriptional regulatory element sequence.

2. An infected PCa cell, wherein the PCa cell has been infected with the genetic probe of claim 1.

3. The infected PCa cell of claim 2, wherein the TfR level on the surface the infected PCa cell is increased from about 10% to about 40% compared to non-infected PCa cell.

4. A composition comprising the infected PCa cell of claim 2.

\* \* \* \* \*